(12) United States Patent
Freire et al.

(10) Patent No.: US 7,560,482 B2
(45) Date of Patent: Jul. 14, 2009

(54) INHIBITORS OF PLASMEPSINS

(75) Inventors: Ernesto Freire, Baltimore, MD (US); Azin Nezami, Baltimore, MD (US); Yoshiaki Kiso, Ibaraki (JP)

(73) Assignee: The Johns Hopkins University, Baltimore, MD (US)

( * ) Notice: Subject to any disclaimer, the term of this patent is extended or adjusted under 35 U.S.C. 154(b) by 733 days.

(21) Appl. No.: 10/471,655

(22) PCT Filed: Mar. 15, 2002

(86) PCT No.: PCT/US02/08024

§ 371 (c)(1),
(2), (4) Date: Sep. 10, 2004

(87) PCT Pub. No.: WO02/074719

PCT Pub. Date: Sep. 26, 2002

(65) Prior Publication Data

US 2005/0037953 A1 Feb. 17, 2005

Related U.S. Application Data

(60) Provisional application No. 60/275,713, filed on Mar. 15, 2001.

(51) Int. Cl.
*A61K 31/366* (2006.01)
*A61K 38/00* (2006.01)
(52) U.S. Cl. .......................... 514/460; 514/12
(58) Field of Classification Search ................... 514/12, 514/460
See application file for complete search history.

(56) References Cited

U.S. PATENT DOCUMENTS

| 5,734,054 | A | 3/1998 | Dolle, III et al. |
| 5,962,506 | A | 10/1999 | Carroll et al. |
| 6,191,277 | B1 | 2/2001 | Dolle, III et al. |

OTHER PUBLICATIONS

Carroll et al. 1998. Identification of Potent Inhibitors of Plasmodium falciparum Plasmepsin II From an Encoded Statine Combinatorial Library, Bioorganic & Medicinal Chemistry Letters, vol. 8, pp. 2315-2320.*

Silva et al. 1996. Structure and inhibition of plasmepsin II, a hemoglobin-degrading enzyme from Plasmodium falciparum (malaria/drug design/crystallography/aspartic protease/cathepsin D), Proc. Natl. Acad. Sci. USA, vol. 93, pp. 10034-10039.*

Haque et al.1999. Potent, Low-Molecular-Weight Non-Peptide Inhibitors of Malarial Aspartyl Protease Plasmepsin II. Journal of Medicinal Chemistry,vol. 42, pp. 1428-1440.*

A. Nezami , E. Freire from the Internstional Journal of Parasitology; "The integration of genomic and structural information in the development of high affinity plasmepsin inhibitors" dated 2002.

A. Nezami et al. artice titled Identification and Characterization of Allophenylnorstatine-Based Inhibitors of Plasmepsin II, an Antimalarial Target dated 2002.

A. Nezami et al. article titled "High-Affinity Inhibition of a Family of *Plasmodium falciparum* Proteases by a Designed Adaptive Inhibitor" dated 2002.

A. Nezami et al.; "The Integration of Genomic and Structural Information in the Development of High Affinity Plasmepsin Inhibitors"; International Journal for Parasitology, vol. 32; 2002; pp. 1669-1676.

A. Nezami et al.; "Identification and Characterization of AllophenyInorstatine-Based Inhibitors of Plasmepsin II, an Antimalarial Target"; Biochemistry, vol. 41, No. 7, 2002; pp. 2273-2280.

A. Nezami et al.; "High-Affinity Inhibition of a Family of *Plasmodium falciparum* Proteases by a Designed Adaptive Inhibitor"; Biochemistry, vol. 42, No. 28, 2003; pp. 8459-8464.

* cited by examiner

*Primary Examiner*—Jon P Weber
*Assistant Examiner*—Kailash C Srivastava
(74) *Attorney, Agent, or Firm*—Whitham, Curtis, Christofferson & Cook, P.C.

(57) ABSTRACT

Compounds and methods for the inhibition of anti-malarial target aspartyl protease plasmepsins (e.g. Plasmepsin I, Plasmepsin II, Plasmepsin IV and HAP) are provided. The compounds are based on allophenylnorstatine substituted at positions R1-R4, such that R1 is isoquinoline, carboxyl, naphtalene, phenyl, phenol, benzene, an amino acid, and derivatives thereof; R2 and R3 are aliphatic groups; and R4 is indan, naphthalene, benzylamine, phenyl, phenol, cyclopentane, tert-butylamine, or derivatives thereof. The compounds may be used to inhibit Plasmepsin II, to kill malarial parasites, and to treat malaria in a patient. Certain of the substituted allophenylnorstatine-based compounds also exhibit inhibitory activity against Cathepsin D.

16 Claims, 20 Drawing Sheets

INHIBITORS OF PLASMEPSINS

This application claims benefit of International Patent Application PCT/US02/08024, filed 15 Mar. 2002, which in turn claims benefit of U.S. provisional patent application 60/275,713, filed 15 Mar. 2001. The complete contents of both of these applications is hereby incorporated by reference.

BACKGROUND OF THE INVENTION

1. Field of the Invention

The invention generally relates to plasmepsin inhibitors and the treatment of malaria. In particular, the invention provides methods and compositions for the use of peptidomimetic allophenylnorstatine based inhibitors of the antimalarial target aspartyl protease Plasmepsin II. More generally, the invention provides compounds and methods for inhibiting plasmepsins (e.g. Plasmepsin I, Plasmepsin II, Plasmepsin IV, HAP) which may provide a number of different pharmaceutical and medical benefits.

2. Background of the Invention

Malaria is one of the most serious infectious diseases in the world, affecting close to 300 million individuals each year. It has been estimated that approximately 40% of the world population lives in regions where malaria is endemic. Each year between 1 and 1.5 million people, mainly children, die from malaria, a number that is continuously increasing due to the proliferation of parasites that are resistant to conventional drug therapies (Wyler, 1993). The rapid spread of drug resistant parasites clearly underscores the need for new therapies and consequently the identification of novel targets for drug development. The malaria parasite uses the hemoglobin of the infected victim as a source of nutrients and energy. One of the key enzymes involved in the degradation of hemoglobin is Plasmepsin II, an aspartic protease of 37 kDa. Since the inhibition of this enzyme leads to starvation of the parasite, Plasmepsin II has been acknowledged to be an important target for the development of new antimalarials.

Four species of protozoan parasites of the genus *Plasmodium* (*P. falciparum, P. vivax, P. malariae* and *P. ovale*) are responsible for malaria in humans; *P. vivax* is the most common but *P. falciparum* causes the most fatalities (Butler et al., 1997; Miller et al., 1994). The *Plasmodium* parasite invades red blood cells and consumes tip to 75% of their hemoglobin content (Goldberg, 1993). The process takes place in an acidic digestive vacuole in the parasite. Three enzymes that digest hemoglobin have been identified in the food vacuole, one cysteine protease (falcipain) and two aspartic proteases (Plasmepsin I and Plasmepsin II) (Francis et al., 1997b). The inhibition of any of these enzymes leads to the starvation of the parasite and has been proposed as a viable strategy for drug development Plasmepsin I and Plasmepsin II are 73% sequence identical. They have different substrate specificities and both contribute to the degradation of hemoglobin. Plasmepsin I is synthesized and processed to a mature form soon after the parasite invades the red blood cell, while the appearance of Plasmepsin II occurs later in development (Francis et al., 1997a). The expression and production of active recombinant Plasmepsin I has been shown to be difficult, yielding a truncated protein that lacks the kinetic properties of the native enzyme (Luker et al., 1996). Plasmepsin U, on the other hand, has been successfully expressed, the recombinant protein behaves identically to the protein isolated from the parasite and its high resolution structure has been determined by x-ray crystallography (Luker et al., 1996; Silva et al., 1996). For those reasons, Plasmepsin II is the target of choice for structure-based drug design, even though the targeting of Plasmepsin I and other plasmepsins is also expected.

Plasmepsin II is a protein of 37 kDa (329 amino acids). The crystallographic structure of Plasmepsin II in complex with the generic statine-based aspartic protease inhibitor pepstatin A (IvaValValStaAlaSta) has been obtained at 2.7 Å for the *Plasmodium falciparum* enzyme (pdb file 1 sme) (Silva et al., 1996) and 2.5 Å for the *Plasmodium vivax* enzyme (pdb file 1 qs8). Plasmepsin II has the typical bilobal structure and topology of eukaryotic aspartic proteases. The active site is located at the interface between the two lobes and is partially covered by a characteristic β-hairpin structure known as the flap. The secondary structure of Plasmepsin II is predominantly beta with only a small fraction (~10%) of amino acids in alpha-helix. Even though pepstatin A and other related statine-containing peptides are known to inhibit Plasmepsin II and other aspartic proteases, very few non-peptidic inhibitors have been described. A common problem with these inhibitors is their poor selectivity and discrimination versus the human aspartic protease Cathepsin D. Cathepsin D is a human protease in the endosomal-lysosomal pathway involved in lysosomal biogenesis and protein targeting, it has 35% overall sequence homology and even higher binding site homology with Plasmepsin II, thus representing a target that needs to be avoided in the development of Plasmepsin II inhibitors.

Allophenylnorstatine-based compounds have been described before in relation to the development of HIV-1 protease inhibitors (Kiso, 1996; Kiso, 1998; Kiso et al., 1999; Mimoto et al., 1999). These compounds are characterized by containing a unique unnatural amino acid, allophenylnorstatine ((2S,3S)-3-amino-2-hydroxy-4-phenylbutyric acid) containing a hydroxymethylcarbonyl isostere. Some of these compounds have been shown to be high affinity inhibitors of the HIV-1 protease, they have low toxicity and excellent bioavailability (Kiso, 1996; Kiso, 1998; Kiso et al., 1999; Mimoto et al., 1999).

SUMMARY OF THE INVENTION

The present invention provides compounds and methods for their use to treat malaria. The compounds work by inhibiting plasmepsins, aspartyl proteases of the malarial parasite that are essential for the parasite's survival. Examples of the Plasmepsins are, for example. Plasmepsin I, Plasmepsin II, Plasmepsin IV, and HAP. Methods are also provided for inhibiting Plasmepsin proteases, and for killing malarial parasites.

The compounds themselves are synthesized based on the allophenylnorstatine "scaffolding" with various functional groups being substituted at positions R1, R2, R3 and R4 of the structure. R1 is A or A-B, wherein A may be a linear or branched aliphatic hydrocarbon having 1-7 carbon atoms which may be substituted by at least one carboxyl group; a 6-membered monocyclic hydrocarbon which may be substituted with a substituent selected from the group consisting of alkyl amino, alkylamino, arylamino, hydroxy, alkyloxy and halogen atom; a bicyclic hydrocarbon having 7-10 carbon atoms which may be substituted by a substituent selected from the group consisting of alkyl, amino, alkylamino, arylamino, hydroxy, alkyloxy and halogen atom; or a monocyclic or bicyclic hydrocarbon wherein more than one carbon atom is substituted; and B is —CO—NH—CH(Ra)—, —CH$_2$—CO—NH(Ra)—, —O—CH$_2$—CO—NH—CH (Ra)—, —OCH$_2$— and —CH$_2$O, where Ra is a linear or branched aliphatic hydrocarbon having 1-7 carbon atoms that may be substituted with a substituent such as alkylthio, hydroxy, aromatic hydrocarbons, and carbamoyl; R2 is hydrogen or a linear or branched aliphatic hydrocarbon having 1-6 carbons; R3 is hydrogen or a linear or branched aliphatic hydrocarbon having 1-6 carbons; and R4 is a linear or branched aliphatic hydrocarbon having 1-10 carbons which can be substituted with a substituent such as aryl, hydroxyl, alkyloxy, amino, alkylamino and halogen; a monovalent moiety derived from an aromatic mono- or bicyclic hydrocarbon having 12 or fewer carbons, and wherein said moiety can be substituted by a substituent such as alkyl, aryl, hydroxyl, allkyloxy, amino, alkylamino, or halogen; a monovalent moiety derived from a heterocycle in which more than one carbon atom is substituted with a hetero atom, in which the moiety can be substituted by a substituent such as alkyl, aryl, hydroxyl, alkyloxy, amino, alkylamino, and halogen.

In preferred embodiments, A is: HOOC—CRbRb—CRbRb—wherein Rb is hydrogen or methyl; phenyl; 3-hydroxy-2-methylphenyl; 2,6-dimethylphenyl; 3-chlorophenyl; 3-phenylaminophenyl; 3-dimethylaminophenyl; 1-naphtyl; 2-naphtyl; 2-pyridyl; 5-isoquinolyl; 2-quinolyl; 2-benzofuranyl; and 2-chromonyl; and B is —CO—NH—CH(Ra)—, —CH$_2$—CO—NH(Ra)—, —O—CH$_2$—CO—NH—CH(Ra)—, —OCH$_2$— or —CH$_2$O, wherein Ra is propyl, isopropyl, isobutyl, sec-butyl, methylthiomethyl, methylthioethyl, methylthiomethyl, phenylmethyl, carbamoylethyl, or 1-hydroxyethyl; R2 is hydrogen or methyl; R3 is hydrogen or methyl; and R4 is benzyl; tert-butyl; 2-hydroxybenzyl; 3-hydroxybenzyl; 4-hydroxybenzyl; 2-hydroxyindanylyl; 2-hydroxy-1-phenethyl; 1-indanyl; 2-methoxybenzyl; 3-methoxybenzyl; 4-methoxybenzyl; 4-methoxyphenethyl; 2-methylbenzyl; 3-methylbenzyl; 4-methylbenzyl; naphtyl; and 1-phenethyl.

In yet another preferred embodiment, the allophenylnorstatine-based compound is a di-peptide and R1 is methylphenol, methylated derivatives of carboxyl, or chlorobenzene. Alternatively, the allophenylnorstatine-based compound may be a tri-peptide, in which case R1 may be methylphenol, methylated derivatives of carboxyl, chlorobenzene, valine, leucine, isoleucine, methionine, phenylalanine, glutamine, or derivatives thereof. In preferred embodiments, R2 and R3 are hydrogen, methyl or ethyl, and R4 is aminoindanol. In yet another embodiment, the allophenylnorstatine-based compound is a tri-peptide and: R1 is isoquinolineoxyacetyl at position P3 and methylthioalanine at position P2, R2 and R3 are methyl, and R4 is (1S,2R)-aminoindanol or tert-butylamine.

In a preferred embodiment, the allophenylnorstatine-based compound exhibits a Ki for Plasmepsin II from *P. falciparum* in the nanomolar to subnanomolar range. Representative allophenylnorstatine-based compounds are KNI-727, KNI-764, KNI-840, KNI-227, KNI-10006, KNI-10026, KNI-10033, KNI-10043 and KNI-10053. The plasmepsin which is inhibited may be Plasmepsin II that originates from a genus of *Plasmodium*, for example, *P. falciparum, P. vivax, P. malariae* or *P. ovale*.

The present invention also provides a method of killing malarial parasites by exposing them to an allophenylnorstatine-based compound in a quantity sufficient to inhibit at least one plasmepsin of the malarial parasite. The malarial parasite may be within a red blood cell and/or within a host, and may be Plasmepsin I, Plasmepsin II, Plasmepsin IV or HAP. The allophenylnorstatine-based compound may be substituted at positions R1, R2, R3 and R4 as described above for inhibiting plasmepsins. Examples of the allophenylnorstatine-based compounds include KNI-727, KNI-764, KNI-840, KNI-227, KNI-10006, KNI-10026, KNI-10033, KNI-10043 and KNI-10053. The malarial parasite may be from *P. falciparum, P. vivax, P. malariae* or *P. ovale*.

The present invention also provides a method of treating malaria which comprises administering a quantity of an allophenylnorstatine-based compound sufficient to alleviate the symptoms of malaria. The allophenylnorstatine-based compound may be substituted at positions R1, R2, R3, and R4 as described above for inhibiting plasmepsins. Examples of such compounds include KNI-727, KNI-764, KNI-840, KNI-227, KNI-10006, KNI-10026, KNI-10033, KNI-10043 and KNI-10053. In a preferred embodiment, the allophenylnorstatine-based compound has high selectivity for plasmepsin rather than cathepsin D.

The present invention also provides a method of inhibiting the enzyme cathepsin D, comprising, exposing the enzyme to an allophenylnorstatine-based compound. The allophenylnorstatine-based compound may be substituted at positions R1, R2, R3 and R4. R1 may be 2,6-dimethylphenyl-OCH$_2$— or 5-isoquinolyl-O—CH$_2$—CO—NH—CH(Ra)— in which Ra is methylthiomethyl; R2 may be methyl or hydrogen; R3 may be methyl or hydrogen: and R4 may be (1S,2R)-2-hydroxyindanyl; (S)-2-hydroxy-1-phenethyl; (S)-indanyl; or (R)-1-phenethyl. Exemplary compounds include KNI-391, KNI-10033, KNI-10006 and KNI-840.

The present invention also provides compositions of matter in the form of compounds KNI-10006 (FIG. 3J); KNI-10007 (FIG. 4A); KNI-10026 (FIG. 4G); KNI-10031 (FIG. 5B); KNI-10033 (FIG. 5D); and KNI-10061, and KNI-10062 (FIGS. 10A and B).

DETAILED DESCRIPTION OF THE PREFERRED
EMBODIMENTS OF THE INVENTION

Figure 1A:
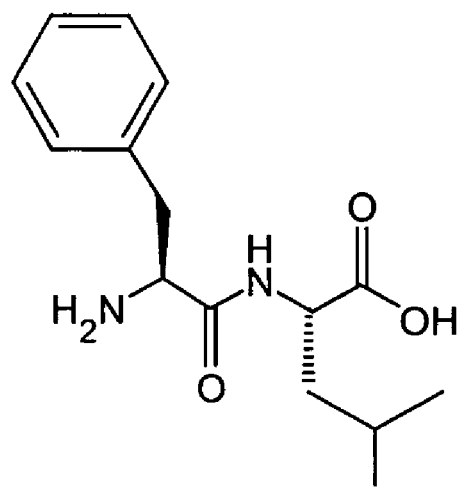
FIG. 1. Chemical structures of: A, Phe-Leu, the cleavage motif of plasmepsin II, and B, the allophenylnorstatine scaffold indicating the places (R1-R4) where different chemical functional groups can be introduced.

The present invention is based on Applicant's discovery that allophenylnorstatine-based compounds are powerful and selective inhibitors of Plasmepsin aspartyl proteases, which are superb anti-malarial targets. The allophenylnorstatine core (FIG. 1B) resembles the Phe-Leu motif (FIG. 1A) that defines the main substrate for plasmepsin II in the human hemoglobin molecule.

The present invention thus provides a method of inhibiting plasmepsins (e.g. the enzyme plasmepsin II) by exposing the enzyme to at least one allophenylnorstatine-based compound. By allophenynorstatine-based compound we mean a compound with the basic "scaffoldinig" structure depicted in FIG. 1B. Compounds which are based on this structure are those which have been synthesized with various moieties or functional groups substituted at positions R1-R4 of the scaffolding. Depending on the exact nature of the substitutions, the resulting compound may be di- or tri-peptidic in nature. Using standard enzymatic nomenclature, if the inhibitor is tripeptidic in nature, then the allophenylnorstatine moiety in these compounds corresponds to the P1 position, R1 corresponds to the P2 position, the thioproline group together with R2 and R3 correspond to the P1' position, and R4 corresponds to the P2' position. If the inhibitor is tripeptidic, either by virtue of R1 being substituted with an amino acid or with a group that, in bonding to the R1 site, forms a third peptide bond, then R1 may correspond to both the P2 and P3 positions.

Applicants have discovered that, in particular, the following substitutions yield allophenylnorstatine compounds with especially useful plasmepsin inhibitory characteristics: R1 is A or A-B, wherein A may be a linear or branched aliphatic hydrocarbon having 1-7 carbon atoms which may be substituted by at least one carboxyl group; a 6-membered monocyclic hydrocarbon which may be substituted with a substituent selected from the group consisting of alkyl, amino, alkylamino, arylamino, hydroxy, alkyloxy and halogen atom; a bicyclic hydrocarbon having 7-10 carbon atoms which may be substituted by a substituent selected from the group consisting of alkyl amino, alkylamino, arylamino, hydroxy, alkyloxy and halogen atom; or a monocyclic or bicyclic hydrocarbon wherein more than one carbon atom is substituted; and B is —CO—NH—CH(Ra)—, —CH$_2$—CO—NH(Ra)—, —O—CH$_2$—CO—NH—CH(Ra)—, —OCH$_2$— and —CH$_2$O, where Ra is a linear or branched aliphatic hydrocarbon having 1-7 carbon atoms that may be substituted with a substituent such as alkylthio, hydroxy, aromatic hydrocarbons, and carbamoyl; R2 is hydrogen or a linear or branched aliphatic hydrocarbon having 1-6 carbons; R3 is hydrogen or a linear or branched aliphatic hydrocarbon having 1-6 carbons; and R4 is a linear or branched aliphatic hydrocarbon having 1-10 carbons which can be substituted with a substituent such as aryl, hydroxyl, alkyloxy, amino, alkylamino and halogen; a monovalent moiety derived from an aromatic mono- or bicyclic hydrocarbon having 12 or fewer carbons, and wherein said moiety can be substituted by a substituent such as alkyl, aryl, hydroxyl, alkyloxy, amino, alkylamino, or halogen; a monovalent moiety derived from a heterocycle in which more than one carbon atom is substituted with a hetero atom, in which the moiety can be substituted by a substituent such as alkyl, aryl, hydroxyl, alkyloxy, amino, alkylamino, and halogen.

In preferred embodiments, A is: HOOC—CRbRb—CRbRb— wherein Rb is hydrogen or methyl; phenyl; 3-hydroxy-2-methylphenyl; 2,6-dimethylphenyl; 3-chlorophenyl; 3-phenylaminophenyl; 3-dimethylaminophenyl; 1-naphtyl; 2-naphtyl; 2-pyridyl; 5-isoquinolyl; 2-quinolyl; 2-benzofuranyl; and 2-chromonyl; and B is —CO—NH—CH(Ra)—, —CH$_2$—CO—NH(Ra)—, —O—CH$_2$—CO—NH—CH(Ra)—, —OCH$_2$— or —CH$_2$O, wherein Ra is propyl, isopropyl, isobutyl, sec-butyl, methylthiomethyl, methylthioethyl, ethylthioethyl, phenylmethyl, carbamoylethyl, or 1-hydroxyethyl; Rat is hydrogen or methyl; R3 is hydrogen or methyl; and R4 is benzyl; tert-butyl; 2-hydroxybenzyl; 3-hydroxybenzyl; 4-hydroxybenzyl; 2-hydroxyindanylyl; 2-hydroxy-1-phenethyl; 1-indanyl; 2-methoxybenzyl; 3-methoxybenzyl; 4-methoxybenzyl; 4-methoxyphenethyl; 2-methylbenzyl; 3-methylbenzyl; 4-methylbenzyl; naphtyl; and 1-phenethyl.

Those of skill in the art will recognize that, by the term "derivatives" we mean functional groups which are modified or substituted by the addition of one or more of certain other typically low (e.g. about MW 100 or less) molecular weight species e.g. by the addition of methyl, benzyl, amine, hydroxyl, acetyl, halogen, thiol, alkyl, aryl, alkyloxy, alkylamino, carbamoyl, carboxyl groups and the like. Similarly, a compound that is "derived from" is one that is the result of such a modification. Specific examples of moieties or functional groups which may be substituted at position R1 include but are not limited to: methylphenol, methylated variations of a carboxylic acid group, isoquinoline, naphthalene, chlorobenzene and phenyl in both di- and tri-peptide mimetics; and valine, isoleucine, methionine, leucine, phenylalanine, and glutamine in tri-peptide mimetics. Examples of moieties or functional groups which may be substituted at position R2 include but are not limited to: hydrogen, methyl and ethyl, moieties. Functional groups which may be substituted at position R3 include but are not limited to: hydrogen, methyl and ethyl. Moieties or functional groups which may be substituted at position R4 include but are not limited to: various benzylamine derivatives, aminoindanol, tert-butylamine, phenol, naphthalene, cyclopentane and indan.

In a preferred embodiment of the present invention, the groups which are substituted at position R1 are as follows: a P3 moiety of isoquinolineoxyacetyl and a P2 moiety of methylthioalanine in the case of tri-peptide mimetics, or a P2 moiety of dimethylphenoxyacetyl or methylphenol in the case of di-peptide mimetics. In a preferred embodiment of the present invention, the group which is substituted at positions R2 and R3 is a methyl group. In a preferred embodiment of the present invention, the groups which are substituted at position R4 are (1S,2R)-aminoindanol or tert-butylamine.

Those of skill in the art will recognize that the methods for synthesizing such compounds are well-established and accessible. For example, see Kiso, 1996; Mimoto et al., 1999.

Specific examples of the compounds which are substituted in this manner include those which exhibit a particularly low Ki value (e.g. KNI-10006, KNI-10030, KNI-10033) and those which exhibit a particularly low Ki value and high selectivity or discrimination for Plasmepsin II compared to Cathepsin D (e.g. KNI-727, KNI-227).

In a preferred embodiment of the present invention, the standard "Plasmepsin II" for determining Ki values is derived from *Plasmodium falciparum*. i.e. the protease is the product of a gene which was originally cloned from *Plasmodium*

*falciparum*. However, those of skill in the art will recognize that the exact source of the Plasmepsin II which is utilized to establish Ki values of the compounds of the present invention is not a key feature of the invention in that Plasmepsin II from a different *Plasmodium* species, or from various strains of the species, could also be utilized. Any art-recognized Plasmepsin II may be utilized to establish Ki values, so long as a useful correlation may be made between the Ki values obtained and the efficacy of the compound in achieving desirable ends such as killing malaria parasites and treating patients to alleviate symptoms of malaria.

By "low Ki value" we mean a Ki value for the inhibition of Plasmepsin II in the range of picomolar to nanomolar. In a preferred embodiment of the present invention, the Ki value for the compound will be, for example less than about 100 nmolar, and more preferably, less than about 50 nmolar, and even more preferably less than about 10 nmolar.

By having high selectivity or a high "discrimination factor" for Plasmepsin II vs Cathepsin D, we mean that the Ki of the compound for Cathepsin D is at least about 2 fold higher than the Ki of the compound for Plasmepsin II. In a preferred embodiment, the ratio of the Ki's of Cathepsin D to Plasmepsin II is about at least 4, and more preferably about at least 10 or more.

However, those of skill in the art will recognize that the desirability of a compound exhibiting high selectivity for Plasmepsin II can be offset or compensated for if the compound displays a low Ki for Plasmepsin II. This is because the lower the Ki of a compound for Plasmepsin II, the less of the compound must be administered and/or over a shorter period of time, in order to achieve a desired effect, such as inhibiting the enzyme or killing a malarial parasite. Logically, if a very low dose of an inhibitor can be administered, then the side effects (e.g. the inhibition of Cathepsin D) will also be decreased, regardless of the level of selectivity of the compound for Plasmepsin II. For example, compound KNI-10006 displays only a 4-fold "discrimination factor", i.e. the compound has about a 4-fold higher affinity for Plasmepsin II than for Cathepsin D. However, because the Ki is very low (0.5 nmolar), very little of the compound will need to be administered in order to achieve a desired result. Thus, side effects such as the inhibition of Cathepsin D will be minimized. In contrast, KNI-840 also has a discrimination factor of 4, but has a Ki of about 20, which could necessitate the administration of about 40 times as much compound (0.5×40=20) to achieve the same level of inhibition as KNI-10006.

In general, for compounds of the present invention which exhibit Ki's for Plasmepsin II in the range of less than about 10 nanomolar, a discrimination factor may not play an essential role in the efficacy of the compound. For compounds with a Ki for Plasmepsin II in the range of about 10 nmolar to about 100 nmolar, a discrimination factor in the range of about 10 to about 50 should be acceptable.

In a preferred embodiment, the present invention provides methods of inhibiting the enzyme Plasmepsin II. However, the commentary herein concerning Plasmepsin H is similar for other plasmepsins, such as those described in Coombs, et al., 2002. By "Plasmepsin II" we mean the aspartyl protease Plasmepsin 11 originating from any protozoan parasite of the genus *Plasmodium*, for example, from *P. falciparum, P. vivax, P. malariae* or *P. ovale*. By "originating from" we mean that the enzyme was, for example, first detected in, isolated from, or cloned from that organism, regardless of later genetic manipulations. In a preferred embodiment of the present invention, the Plasmepsin II that is inhibited is that of *P. falciparum*. Further, the enzyme to be inhibited may be either naturally occurring within the parasite within a host, naturally occurring within the parasite in a laboratory culturing system, or may have been obtained from the parasite by isolation techniques which are well known to those of skill in the art, or may be obtained from a recombinant gene which encodes the protein. In addition, the term "Plasmepsin II" is meant to include all forms of the protease such as those displaying mutations in the gene (which may or may not be reflected in the primary structure of the protein, such as in naturally-occurring nucleotide polymorphisms) as a result of naturally occurring mutations, variation between and within species or strains, including other genomically-identified plasmepsins, or purposeful (i.e. intentional) or fortuitous mutations which are introduced in a laboratory setting, e.g. during recombinant cloning of the gene. As such forms of Plasmepsin II may be inhibited by the practice of the present invention. In general, any aspartyl protease displaying about 75% or greater, or preferably from about 80% or greater, or most preferably from about 90% or greater amino acid sequence homology with Plasmepsin II from *P. falciparum*, may be inhibited by the methods of the present invention, so long as the substrate specificity of such a protease is close enough to that of Plasmepsin II of *P. falciparum* so that the compounds of the present invention inhibit the protease.

In a preferred embodiment, the allophenylnorstatine-based compound which is utilized to inhibit the Plasmepsin II is substituted at positions R1-R4 such that R1 is 2,6-dimethylphenyl-OCH$_2$—, 3-hydroxy-2-methylphenyl or 5-isoquinolyl-O—CH$_2$—CO—NH—CH(Ra) where Ra is methylthiomethyl; R2 is methyl; R3 is methyl; and R4 is benzyl; tert-butyl; 2-hydroxybenzyl; 3-hydroxybenzyl; (1S,2R)-2-hydroxyindanyl; (1R,2S)-2-hydroxyindanyl; (S)-2-hydroxy-1-phenethyl; (S)-indanyl; 4-methoxyphenethyl; 2-methylbenzyl; 3-methylbenzyl; naphthyl; or (R)-1-phenethyl.

In yet another preferred embodiment, the allophenylnorstatine-based compound winch is utilized to inhibit the Plasmepsin II is substituted at positions R1-R4 such that R1 is isoquinolineoxyacetyl and methylthioalanine in tri-peptides and dimethylphenoxyacetyl or methylphenol in di-peptides, R2 is a methyl group, R3 is a methyl group, and R4 is (1S, 2R)—aminoindanol or tert-butylamine, indan, methylphenyl, or o-benzylamine and the allophenylnorstatine-based compound exhibits a Ki for Plasmepsin II from *P. falciparum* in the nanomolar to subnanomolar range. In yet another preferred embodiment, the allophenylnorstatine-based compound is KNI-727, KNI-764, KNI-840, KNI-227, KNI-10006, KNI-10026, KNI-10033, KNI-10043 or KNI-10053, and the Plasmepsin II originates from a genus of *Plasmodium* selected from the group consisting of *P. falciparum, P. vivax, P. malariae* or *P. ovale*.

The present invention provides methods for treating malaria in a patient in need thereof in order to alleviate symptoms of the disease by administering an allophenylnorstatine-based compound to the patient. In a preferred embodiment, the allophenylnorstatine-based compound which is utilized to treat malaria is substituted at positions R1-R4 as described above for inhibiting plasmepsins. In yet another embodiment, R1 is isoquinolineoxyacetyl and methylthioalanine in tri-peptides and dimethylphenoxyacetyl or methylphenol in di-peptides, R2 is a methyl group, R3 is a methyl group, and R4 is (1S,2R)-aminoindanol or tert-butylamine, indan, methylphenyl, or o-benzylamine, and the allophenylnorstatine-based compound exhibits a Ki for Plasmepsin II from *P. falciparum* in the nanomolar to subnanomolar range. In yet another preferred embodiment, the allophenylnorstatine-based compound which is utilized is KNI-727, KNI-764, KNI-840, KNI-227, KNI-10006, KNI-10026, KNI-10033, KNI-10043 or KNI-10053. The in vivo IC50 for such a compound will generally be in the range of about 0.1 to about 100 µM and preferably below about 10 µM.

Those of skill in the art will recognize that the precise quantity of such a compound to be administered will vary from case to case, and is best determined by a skilled practitioner such as a physician. For example, the amount may vary based on several characteristics of the patient, e.g. age, gender, weight, overall physical condition, extent of disease, and the like. Further, the individual characteristics of the compound itself (e.g. Ki, selectivity, IC50, solubility, bioavailability, and the like) will also play a role in the amount of compound that must be administered. However, in general, the required amount will be such that the concentration of compound in the blood stream of the patient is about equal to the IC50 of the compound. In preferred embodiment of the present, this concentration will be in the range of about 0.1 to about 100 µM, and more preferably below about 10 µM.

The causative agent of the malaria that is treated in a patient according to the methods of the present invention may be any of a variety of *Plasmodium* species which are well-known to those of skill in the art, including but not limited to *P. falciparum, P. vivax, P. malariae* or *P. ovale*, as well as various strains of these species. Further, the species may or may not be already resistant to other forms of treatment, such as treatment with chloroquine.

The compounds which are administered in the practice of the present invention may be administered in any of many forms which are well-known to those of skill in the art. For example, they may be administered in any of a variety of art-accepted forms such as tablets, capsules, various injectable formulations, liquids for oral administration and the like, as suitable for the desired means of administration. The preparation which is administered may include one or more than one inhibitory compound, and may further contain other suitable substances and excipients, including but not limited to physiological acceptable buffering agents, stabilizers (e.g. antioxidants), flavoring agents, agents to effect the solubilization of the compound, and the like. Administration of the compounds may be effected by any of a variety of routes that are well-known to those of skill in the art, including but not limited to oral, perenteral, intravenously, via inhalation, and the like. Further, the compounds may be administered in conjunction with other appropriate treatment modalities, for example, with nutritional supplements, agents to reduce symptoms such as fever, treatment with other anti-malarial agents such as chloroquine, mefloquine, sulphadoxine-pyrimethamine, fansidar, artemisinin, quinine, atovaquone-proguanil, and the like The present invention also provides methods for killing malarial parasites. Malarial parasites which may be killed by the methods of the present invention include but are not limited to *P. falciparum, P. vivax, P. malariae* or *P. ovale*, and various strains thereof. The method is carried out by exposing the parasite to an allophenylnorstatine-based compound in a quantity sufficient to kill the parasite. In preferred embodiments, the allophenylnorstatine-based compound is substituted at positions R1-R4 such that R1 is isoquinolineoxyacetyl and methylthioalanine in tri-peptides and dimethylphenoxyacetyl or methylphenol in di-peptides, R2 is a methyl group, R3 is a methyl group, and R4 is (1S,2R)-aminoindanol or tert-butylamine, indan, methylphenyl, or o-benzylamine. The parasite to be killed may be within a host, or may be in culture. The parasite may be within a red blood cell. In a preferred embodiment, the allophenylnorstatine-based compound used to kill the malarial parasite exhibits a Ki for Plasmepsin II from *P. falciparum* in the nanomolar to subnanomolar range, and may be KNI-727, KNI-764, KNI-840, KNI-227, KNI-10006, KNI-10026, KNI-10033, KNI-10043 or KNI-10053. The IC50 for such a compound will generally be in the range of about 0.1 to 1100 M and preferably below about 10 µM.

The quantity of allophenylnorstatine-based compound required to kill a malarial parasite (and by extension, to treat malaria) can be ascertained in part by determining the IC50 of the compound. Those of skill in the art will recognize that, while in general it may be expected that the IC50 of a compound will be related to its affinity for the enzyme Plasmepsin II, it is also possible that compounds with lesser Ki values will exhibit IC50 values that are more favorable than anticipated based on their Ki values. For example, see the discussion given in Example 5. Such results may be due to any of several factors, such as the ability of the compound to access the targeted protease (i.e. to enter red blood cells), differences in solubility and ADME (absorption, distribution, metabolism and excretion), or other factors. In general, for utilization in the practice of the present invention, an IC50 value in the range of about 0.1 to about 100 µM and preferably below about 10 µM.

Figure 3A:
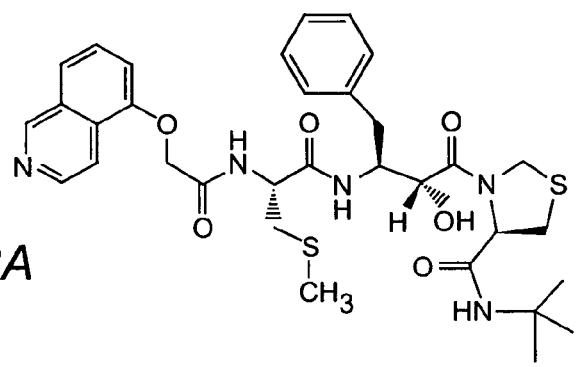
FIG. 3. Chemical structures of: A, KNI-529; B, KNI-840; C, KNI-492; D, KNI-227; E, KNI-10001; F, KNI-10002; G, KNI-10003; H, KNI-10004; I, KNI-10005; and J, KNI-10006.
Figure 3B:
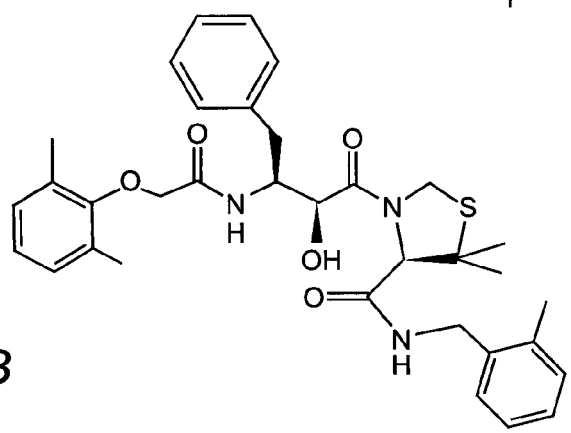
Figure 3C:
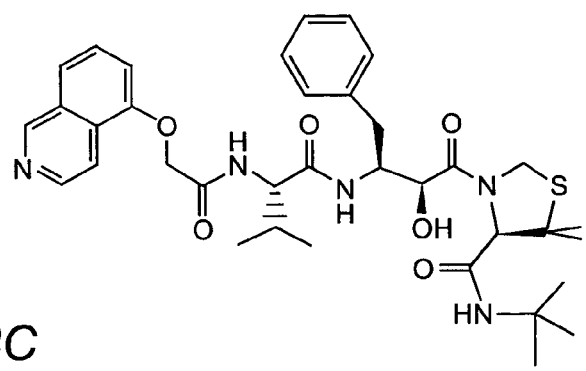
Figure 3D:
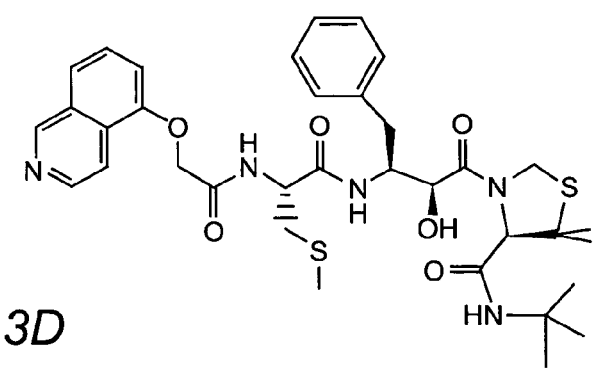
Figure 3E:
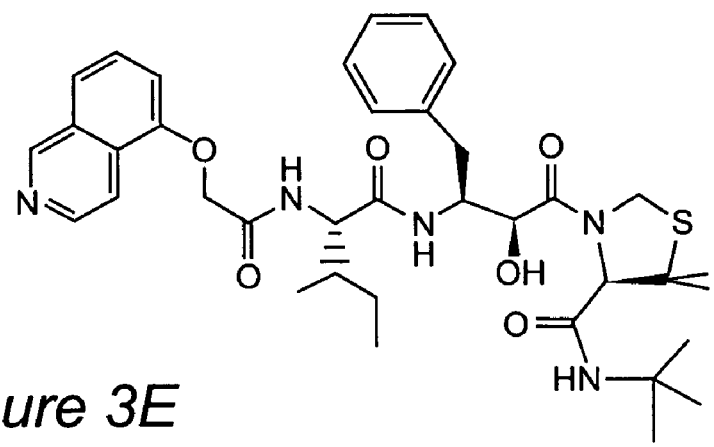
Figure 3F:
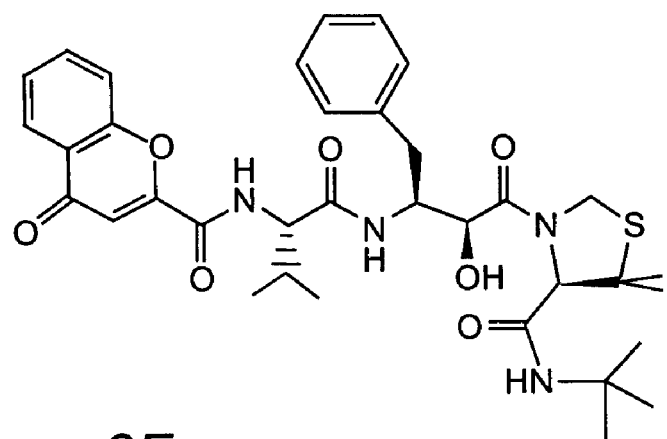
Figure 3G:
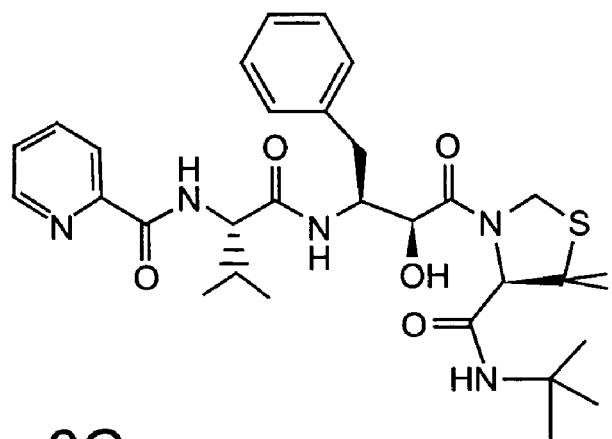
Figure 3H:
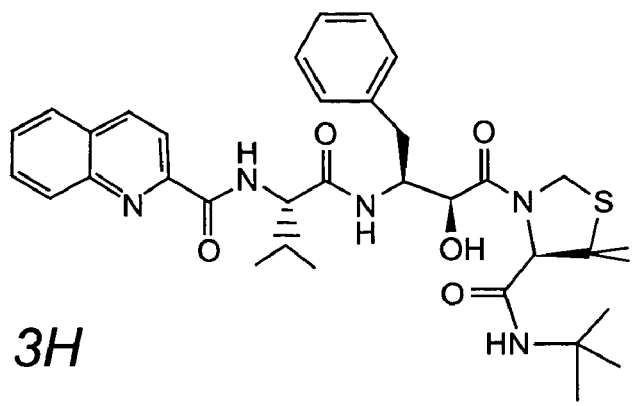
Figure 3I:
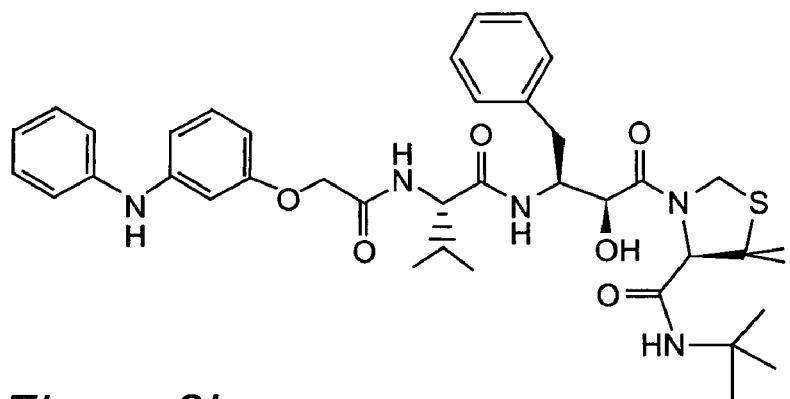
Figure 3J:
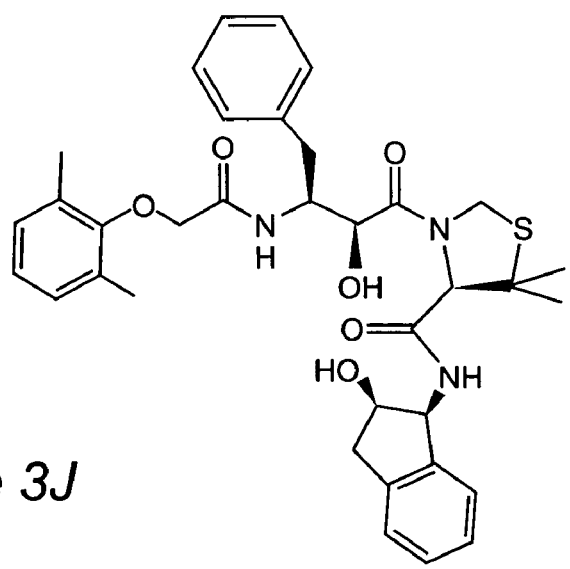
Figure 4A:
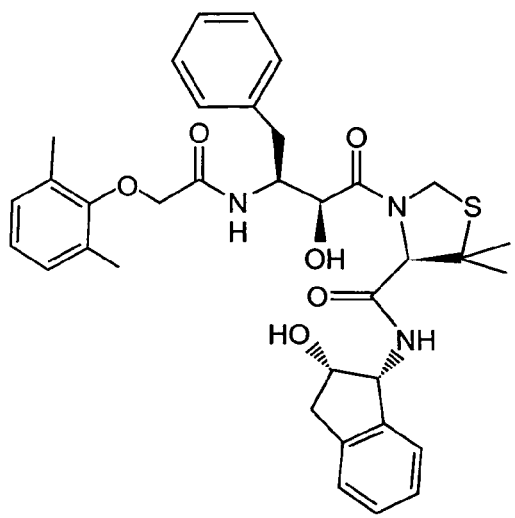
FIG. 4. Chemical structures of: A, KNI-10007; B, KNI-10008; C, KNI-10009; D, KNI-10010; E, KNI-10024; F, KNI-10025; G, KNI-10026; H, KNI-10027; I, KNI-10028; and J, KNI-10029.
Figure 4B:
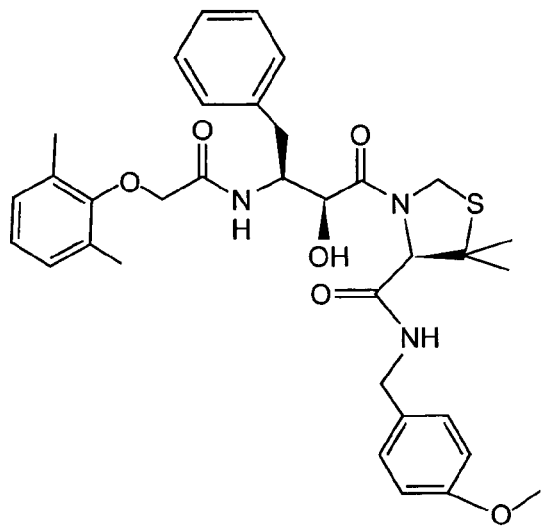
Figure 4C:
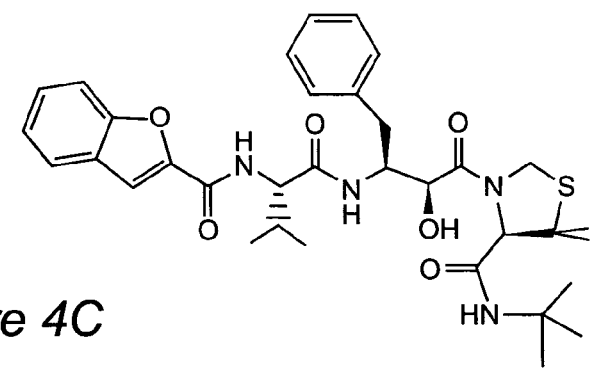
Figure 4D:
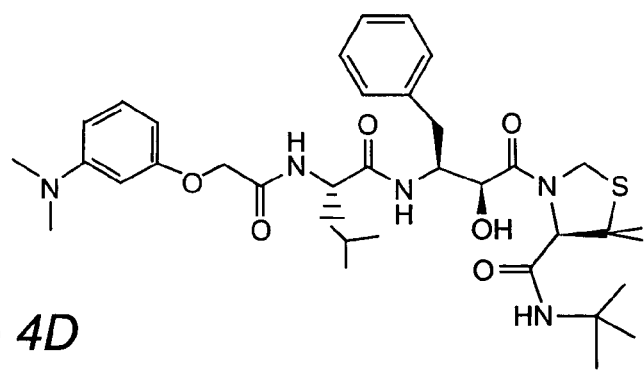
Figure 4E:
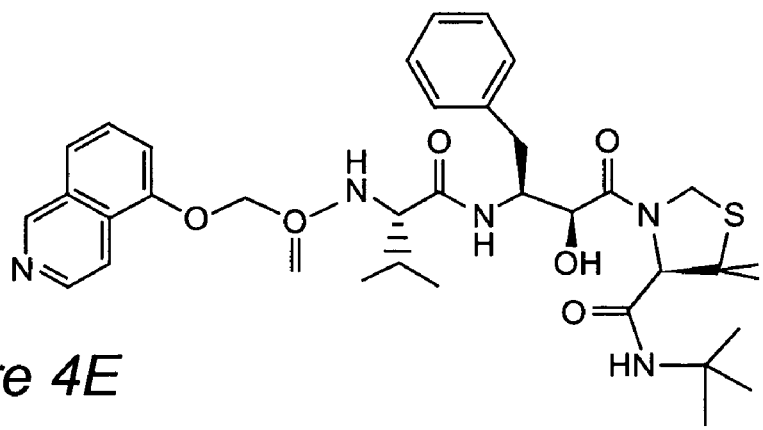
Figure 4F:
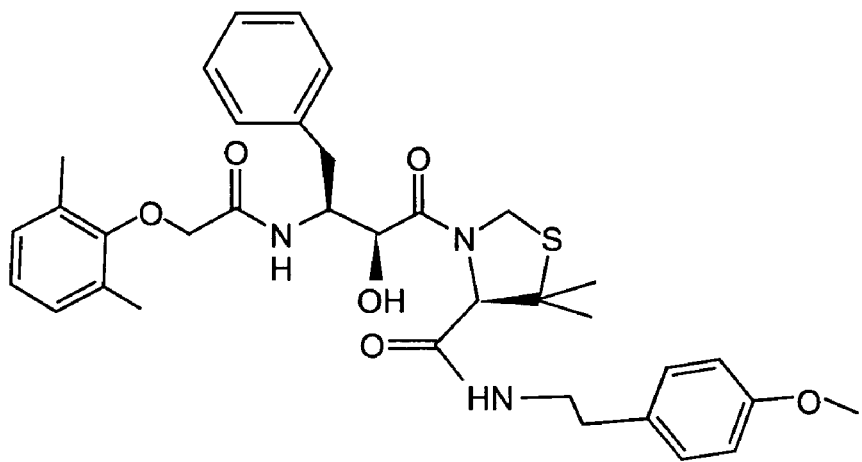
Figure 4G:
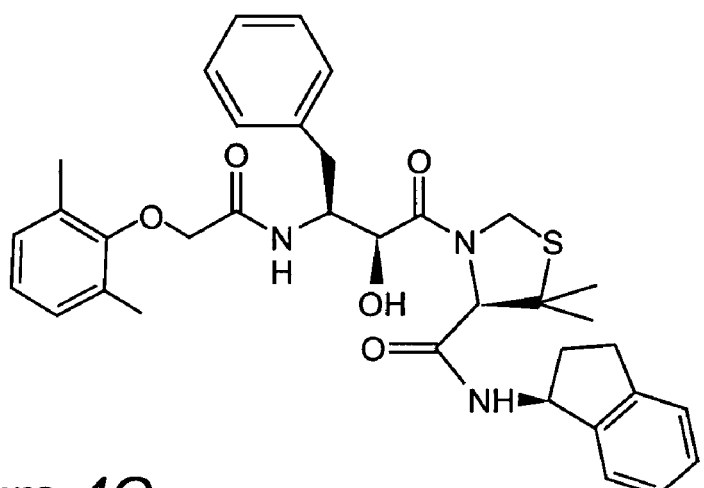
Figure 4H:
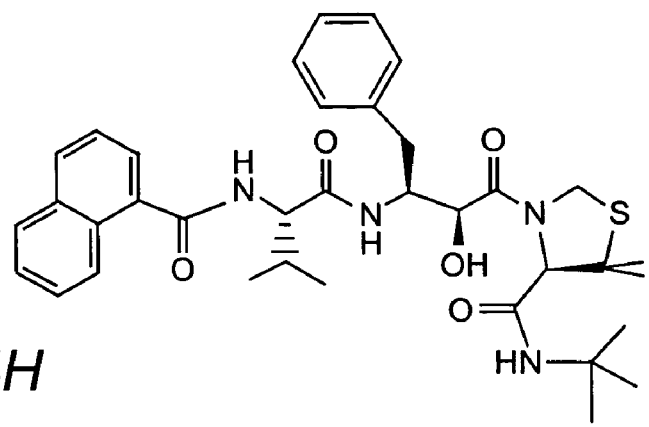
Figure 4I:
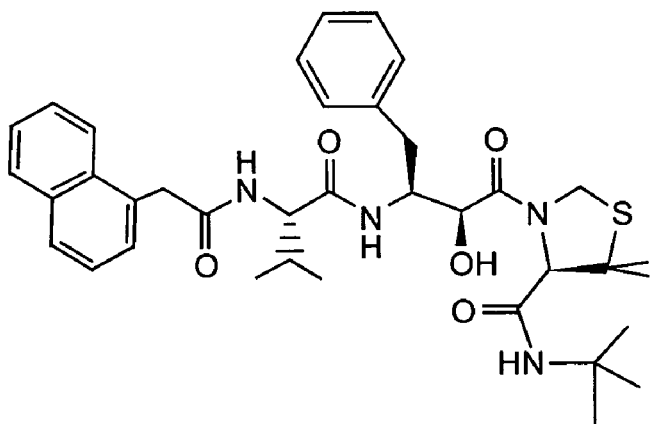
Figure 4J:
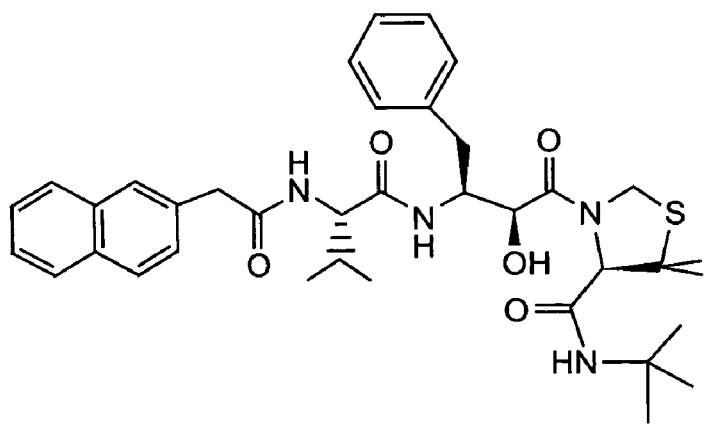
Figure 5A:
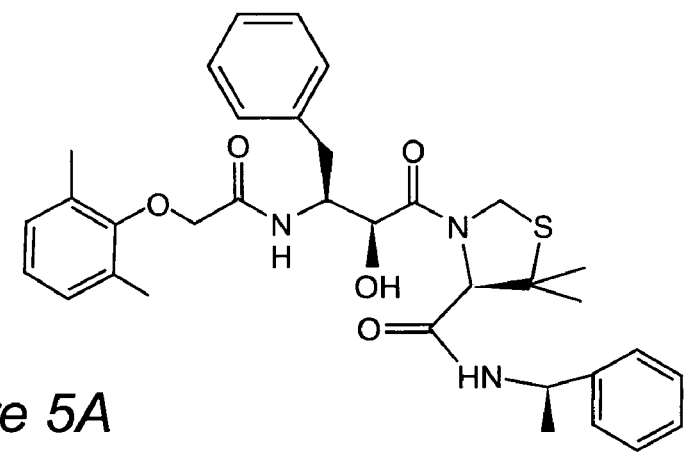
FIG. 5. Chemical structures of: A, KNI-10030; B, KNI-10031; C, KNI-10032; D, KNI-10033; E, KNI-10041; F, KNI-10042; G, KNI-10043; H, KNI-10044; I, KNI-10045; and J, KNI-10046.
Figure 5B:
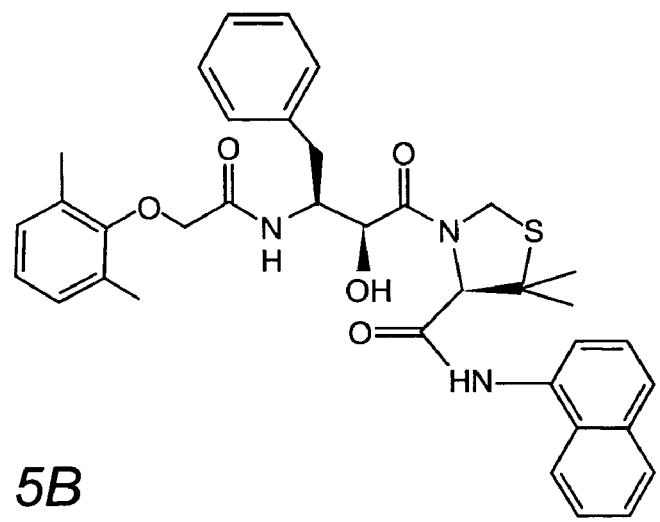
Figure 5C:
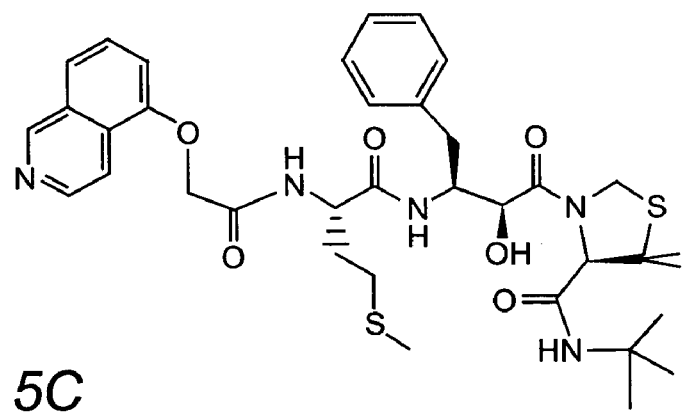
Figure 5D:
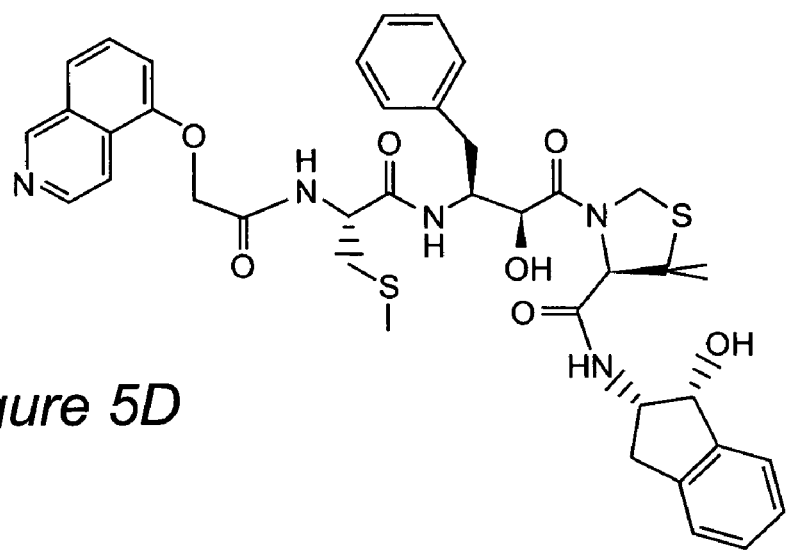
Figure 5E:
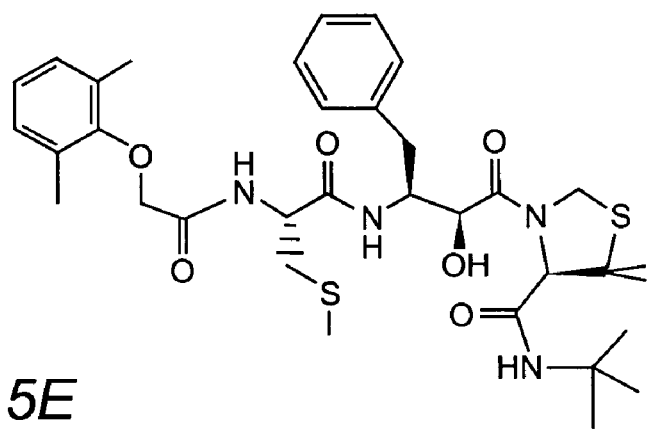
Figure 5F:
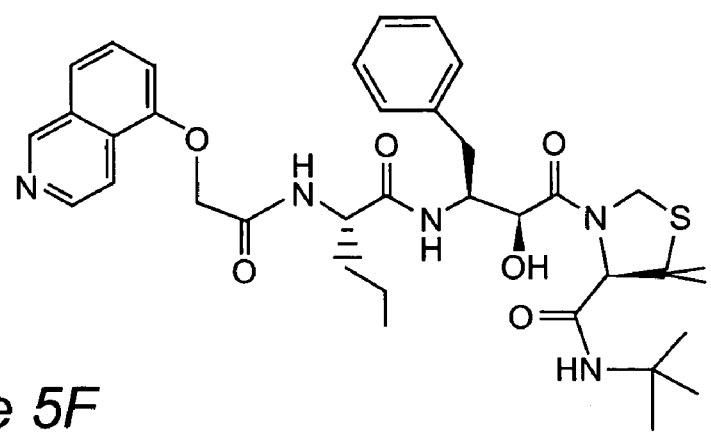
Figure 10A:
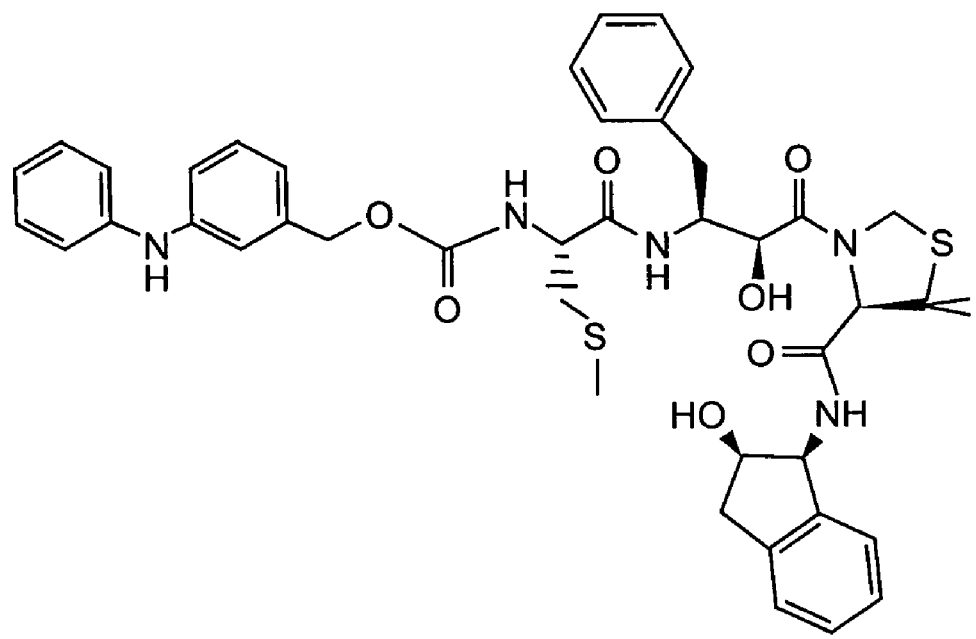
FIGS. 10A and B. Structural representations of A, KNI-10061 and B, 10062.
Figure 10B:
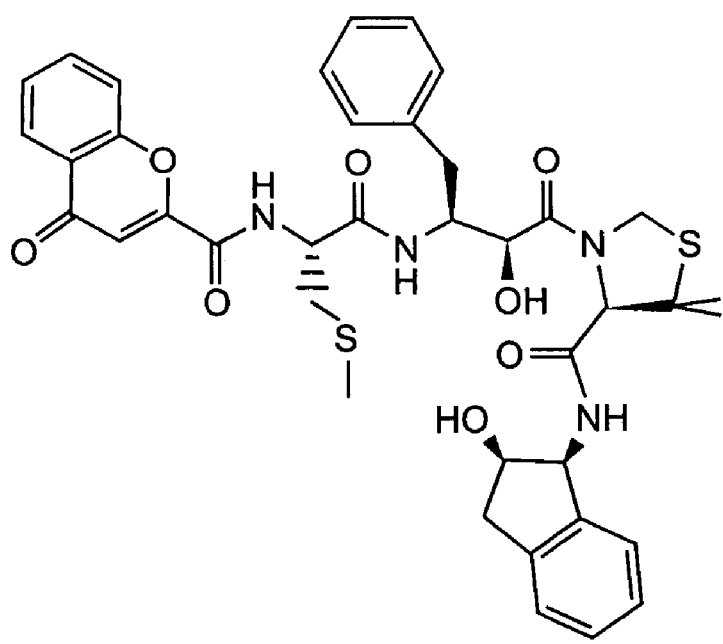

The present invention also provides new compositions of matter. The compositions of matter are allophenylnorstatine-based compounds which are useful for carrying out the methods of the present invention such as inhibiting the plasmepsins, killing malarial parasites, and treating malaria in a patient. The new compositions are represented in this application as: KNI-10006 (FIG. 3J); KNI-10007 (FIG. 4A); KNI-10026 (FIG. 4G); KNI-10031 (FIG. 5B); KNI-10033 (FIG. 5D); and KNI-10061, and KNI-10062 (FIGS. 10A and B).

It is noteworthy that some of the allophenylnorstatine-based compounds are also potent inhibitors of the human enzyme Cathepsin D. Thus, they can be used in applications in which this enzyme needs to be inhibited. The R1-R4 substitution pattern for allophenylnorstatine-based compounds that are good inhibitors of Cathepsin D is: R1 may be 2,6-dimethylphenyl-OCH$_2$— or 5-isoquinolyl-O—CH$_2$—CO—NH—CH(Ra)— in which Ra is methylthiomethyl; R2 may be methyl or hydrogen; R3 may be methyl or hydrogen; and R4 may be (1S,2R)-2-hydroxyindanyl; (S)-2-hydroxy-1-phenethyl; (S)-indanyl; or (R)-1-phenethyl. In a preferred embodiment, when the allophenylnorstatine-based compound is a dipeptide R1 is carboxyl or a derivative of a carboxyl at position P2 and when said allophenylnorstatine-based compound is a tripeptide R1 is chromen-4-one at position P3 or valine at position P3; both R2 and R3 are hydrogen or methyl; and R4 is indanol or tert-butylamine. Specific examples of these compounds are high specificity compounds such as KNI-391 and high affinity compounds such as KNI-10033, the Ki's for Cathepsin D for which are 1.35 and 0.040 µM, respectively, as well as KNI-10006 and KNI-840. In general, in order to be useful as an inhibitor of Cathepsin D, a compound will have a Ki in the picomolar to the nanomolar range.

Applications in which the inhibition of Cathepsin D is useful include but are not limited to the analysis and monitoring of protein catabolism, antigen processing, degenerative diseases, and breast cancer progression.

EXAMPLES

Example 1

Figure 7A:
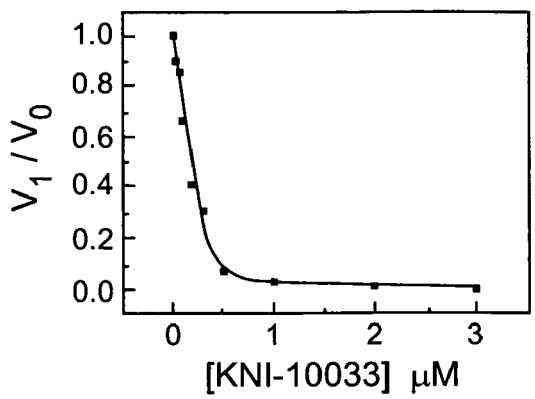
FIG. 7A-C. Inhibition of Plasmepsin II from *Plasmodium falciparum* by KNI-10033, KNI-10030 and KNI-10006 at 20° C. in 10 mM sodium citrate, 100 mM NaCl, 2% DMSO, pH 4.0. The inhibition constants are 3 nM, 11 nM and 0.5 rLM respectively.
Figure 7B:
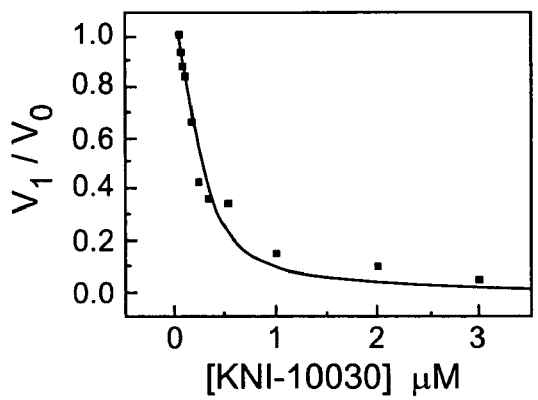
Figure 7C:
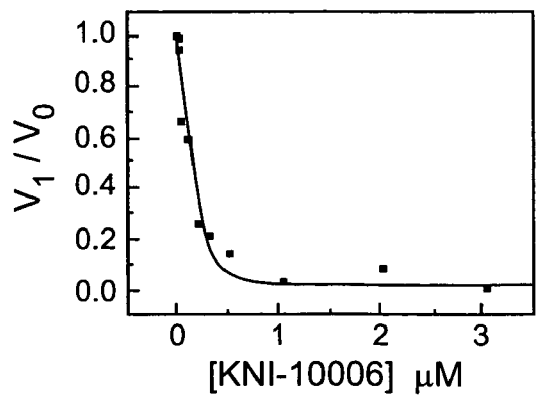

The specific activity of plasmepsin II from *Plasmodium falciparum* (Plm II) cloned in and purified from *Escherchia coli* and commercially available human Cathepsin D were measured by following the hydrolysis of the chromogenic substrate Ala-Leu-Glu-Arg-Thr-nPhe-Phe-Ser-Phe-Pro-Thr-OH (California Peptide Research Inc., Napa, Calif.). The decrease in absorbance upon hydrolysis is monitored at 300 nm. Typical Plasmepsin II preparations hydrolyze chromogenic substrate at 4-5 s$^{-1}$ at 37° C. The inhibition assays were performed at 25° C. in 10 mM sodium formate, 2% DMSO, pH 4.0. These pH conditions mimic the conditions in the food vacuole of the parasite. Under the conditions of the assays the $K_m$ for plasmepsin II is 20 µM and for human Cathepsin D is 130 µM. Inhibition constants ($K_i$) for the inhibitors are obtained at the desired temperature and solvent conditions by measuring the rate of substrate hydrolysis at increasing amounts of inhibitors. Exemplary results from three compounds (KNI-10033, KNI-10030 and KNI-10006) are shown in FIG. 7A-C, and the results obtained with all KNI compounds tested are given in Table 1.

TABLE 1

Allophenylnorstatine-based Compounds Tested for Plasmepsin II Inhibition*

| | Compound | MW | $K_i$ Plm II µM | $K_i$ CatD µM |
|---|---|---|---|---|
| 1 | KNI-272 | 668 | 1.0 ± 0.2 | 2.58 ± 0.30 |
| 2 | KNI-727 | 556 | 0.070 ± 0.040 | 1.60 ± 0.30 |
| 3 | KNI-577 | 528 | 0.590 ± 0.070 | 3.44 ± 0.70 |
| 4 | KNI-391 | 494 | 12.66 ± 1.50 | 1.35 ± 0.08 |
| 5 | KNI-413 | 522 | 1.39 ± 0.50 | 7.26 ± 1.40 |
| 6 | KNI-547 | 494 | 30.7 ± 8.1 | 18.17 ± 3.30 |
| 7 | KNI-549 | 522 | 8.60 ± 1.30 | 37.68 ± 8.20 |
| 8 | KNI-576 | 500 | 9.26 ± 3.60 | 7.03 ± 1.60 |
| 9 | KNI-764 | 576 | 0.030 ± 0.009 | 0.201 ± 0.020 |
| 10 | KNI-357 | 466 | 96.87 ± 19.1 | 8.12 ± 1.50 |
| 11 | KNI-529 | 668 | 8.09 ± 2.60 | 8.82 ± 2.80 |
| 12 | KNI-840 | 604 | 0.020 ± 0.010 | 0.080 ± 0.090 |
| 13 | KNI-492 | 678 | 0.34 ± 0.02 | 3.70 ± 0.35 |
| 14 | KNI-227 | 696 | 0.036 ± 0.01 | 1.773 ± 0.23 |
| 15 | KNI-10001 | 692 | 0.359 ± 0.060 | 1.609 ± 0.330 |
| 16 | KNI-10002 | 665 | 0.244 ± 0.02 | 0.112 ± 0.020 |
| 17 | KNI-10003 | 598 | 1.148 ± 0.190 | 0.97 ± 0.10 |
| 18 | KNI-10004 | 648 | 0.522 ± 0.050 | 0.290 ± 0.090 |
| 19 | KNI-10005 | 718 | 0.250 ± 0.190 | 0.507 ± 0.100 |
| 20 | KNI-10006 | 632 | 0.0005 ± 0.001 | 0.002 ± 0.010 |
| 21 | KNI-10007 | 632 | 0.071 ± 0.010 | 0.806 ± 0.600 |
| 22 | KNI-10008 | 620 | 0.169 ± 0.020 | 0.461 ± 0.140 |
| 23 | KNI-10009 | 637 | 2.183 ± 0.250 | 0.515 ± 0.047 |
| 24 | KNI-10010 | 670 | 0.691 ± 0.040 | 5.66 ± 0.61 |
| 25 | KNI-10024 | 692 | 0.131 ± 0.040 | 0.28 ± 0.05 |
| 26 | KNI-10025 | 634 | 0.075 ± 0.010 | 0.655 ± 0.083 |
| 27 | KNI-10026 | 616 | 0.015 ± 0.005 | 0.105 ± 0.018 |
| 28 | KNI-10027 | 647 | 1.074 ± 0.090 | 1.034 ± 0.200 |
| 29 | KNI-10028 | 661 | 1.628 ± 0.157 | 0.69 ± 0.07 |
| 30 | KNI-10029 | 661 | 0.860 ± 0.090 | 0.282 ± 0.039 |
| 31 | KNI-10030 | 604 | 0.011 ± 0.003 | 0.111 ± 0.015 |
| 32 | KNI-10031 | 626 | 0.083 ± 0.007 | 0.130 ± 0.019 |
| 33 | KNI-10032 | 710 | 0.535 ± 0.055 | 2.62 ± 0.39 |
| 34 | KNI-10033 | 772 | 0.003 ± 0.001 | 0.040 ± 0.010 |
| 35 | KNI-10041 | 673 | 0.496 ± 0.069 | 1.668 ± 0.256 |
| 36 | KNI-10042 | 678 | 0.222 ± 0.017 | 2.263 ± 0.166 |
| 37 | KNI-10043 | 620 | 0.022 ± 0.005 | 0.053 ± 0.008 |
| 38 | KNI-10044 | 620 | 0.532 ± 0.070 | 1.040 ± 0.178 |
| 39 | KNI-10045 | 562 | 1.084 ± 0.165 | 6.158 ± 0.671 |
| 40 | KNI-10046 | 590 | 0.096 ± 0.020 | 0.260 ± 0.023 |
| 41 | KNI-10047 | 606 | 0.055 ± 0.007 | 0.252 ± 0.053 |
| 42 | KNI-10048 | 606 | 0.099 ± 0.014 | 0.771 ± 0.097 |
| 43 | KNI-10049 | 627 | 1.511 ± 0.125 | 2.580 ± 0.682 |
| 44 | KNI-10050 | 680 | 2.625 ± 0.281 | 38.10 ± 1.87 |
| 45 | KNI-10051 | 726 | 0.186 ± 0.014 | 6.512 ± 1.224 |
| 46 | KNI-10052 | 604 | 0.572 ± 0.054 | 1.321 ± 0.152 |
| 47 | KNI-10053 | 604 | 0.041 ± 0.009 | 0.360 ± 0.054 |
| 48 | KNI-10054 | 606 | 0.273 ± 0.041 | 1.642 ± 0.146 |
| 49 | KNI-10055 | 707 | 1.172 ± 0.071 | 6.279 ± 0.981 |
| 50 | KNI-10056 | 627 | 1.773 ± 0.154 | 1.283 ± 0.161 |
| 51 | KNI-10057 | 710 | 0.428 ± 0.021 | 5.295 ± 0.633 |

*Inhibition constants ($K_i$) were obtained by fitting the data to the standard equations for competitive inhibition.

As can be seen, the inhibition results indicate that several of the compounds, KNI-727, KNI-764, KNI-840, KNI-227, KNI-10006, KNI-10026, KNI-10033, KNI-10043 and KNI-10053 have inhibition constants against Plasmepsin 11 in the nanomolar and subnanomolar range (also see Table 2, column 2). This Example demonstrates that allophenylnorstatine-based compounds that are substituted such that R1 is isoquinolineoxyacetyl and methylthioalanine in tri-peptides and dimethylphenoxyacetyl or methylphenol in di-peptides, R2 is a methyl group, R3 is a methyl group, and R4 is (1S,2R)-aminoindanol or tert-butylamine, indan, methylphenyl, or o-benzylamine, are powerful inhibitors of Plasmepsin II.

Example 2

Ratio of Inhibition Constants for Plasmepsin II Versus Cathepsin D

Figure 8A:
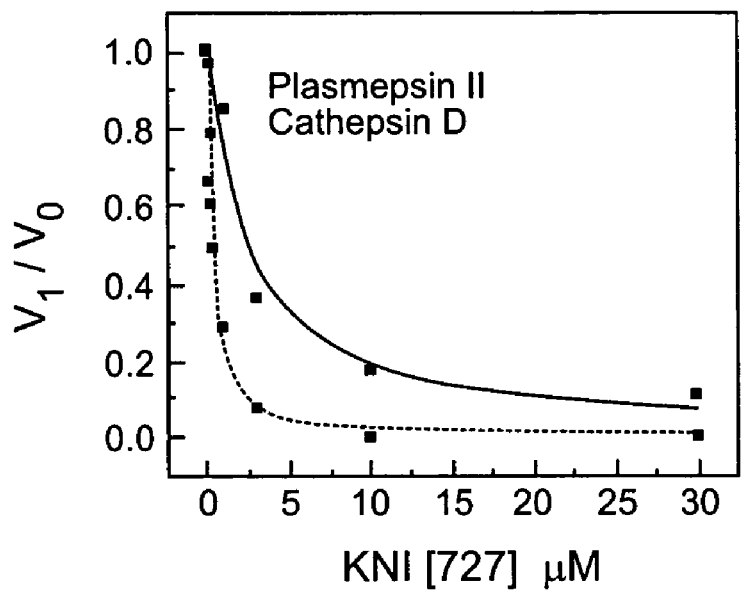
FIGS. 8A and B. A and B: KNI inhibitors with high affinity for Plasmepsin II and high selectivity between Plasmepsin II and human Cathepsin D. A, KNI-227 and B, KNI-727 have K$_i$s of 30 and 70 nM against Plasmepsin II and Cathepsin D selectivities of 50 and 22 respectively.
Figure 8B:
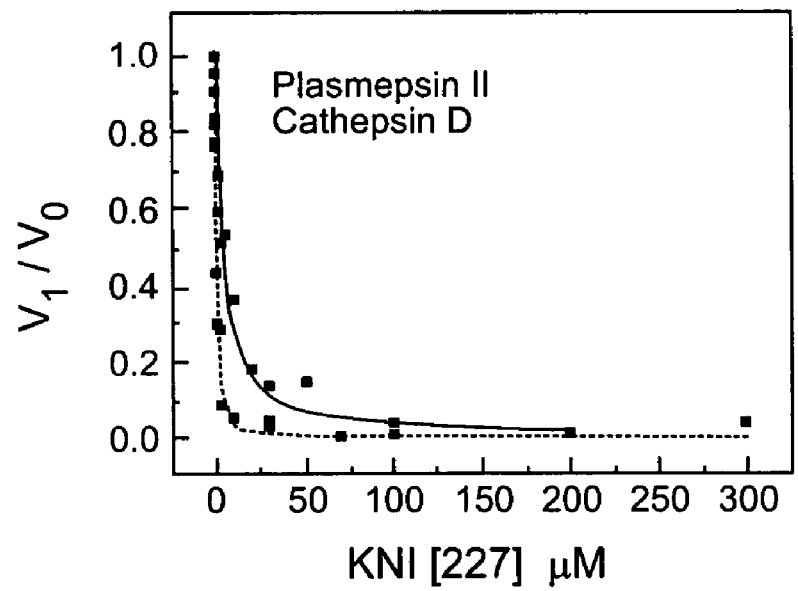

As described above, it is preferable that the inhibitors display not only strong inhibition of Plasmepsin II, but that they display selectivity for that enzyme. The results of a comparison of inhibition curves for two compounds, KNI-227 and KNI-727, are given in FIGS. 8A and B. Column 4 of Table 2 gives the numerical values of a comparison of the inhibition constants of the indicated KNI-compounds for Plasmepsin 11 versus Cathepsin D. The values given represent the ratio of the Ki for Cathepsin D to the for Plasmepsin II, i.e. the discrimination factor. As can be seen, the selected KNI compounds show a range of from about 2 to about 50 fold selectivity for Plasmepsin II over Cathepsin D.

This example demonstrates that KNI compounds have the ability to strongly inhibit plasmepsin II while discriminating against Cathepsin D in order to achieve high selectivity.

TABLE 2

Comparison of $K_i$'s for Plasmepsin II and Cathepsin D

Figure 2A:
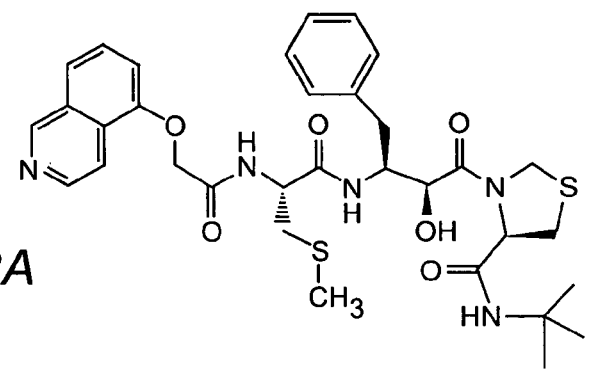
FIG. 2. Chemical structures of: A, KNI-272; B, KNI-727; C, KNI-577; D, KNI-391; E, KNI-413; F, KNI-547; G, KNI-549; H, KNI-576; I, KNI-764; and J, KNI-357.
Figure 2B:
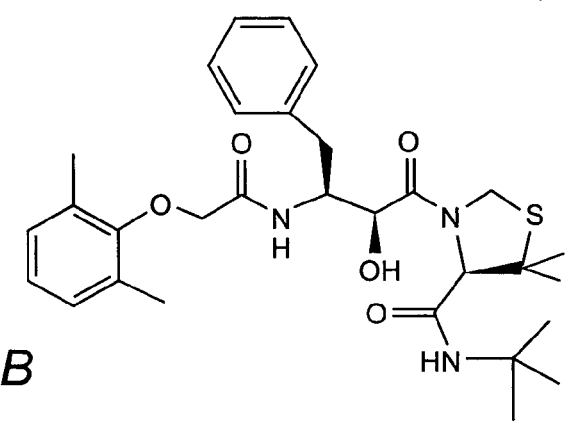
Figure 2C:
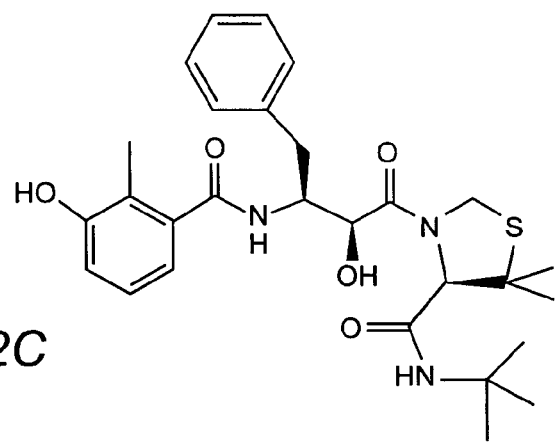
Figure 2D:
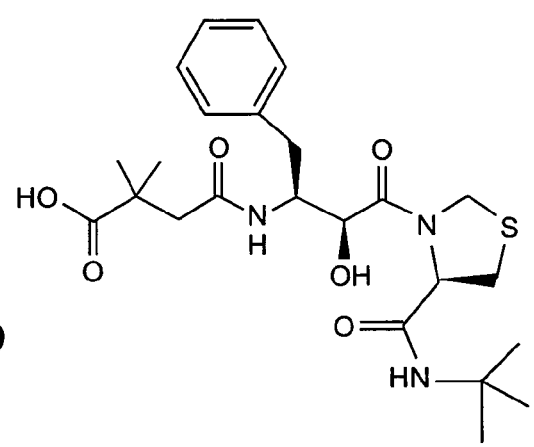
Figure 2E:
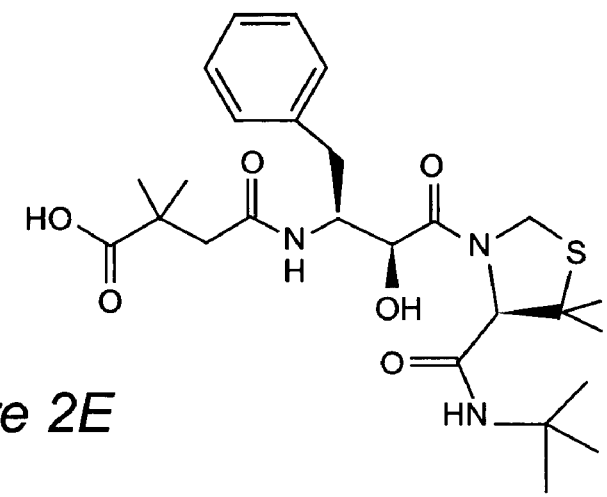
Figure 2F:
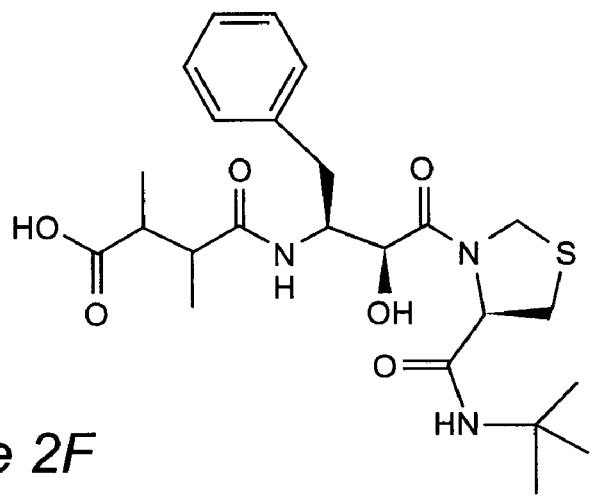
Figure 2G:
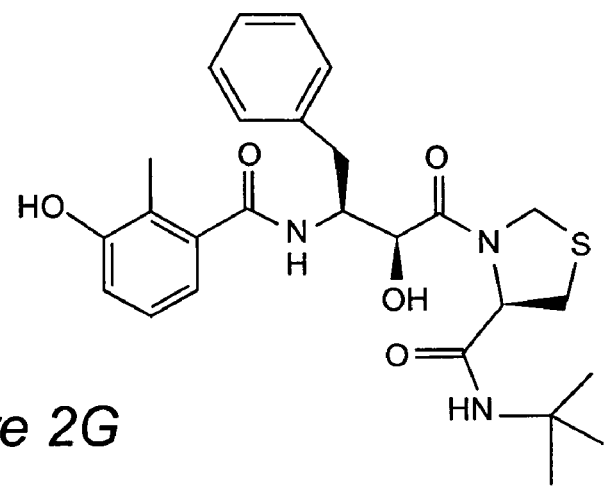
Figure 2H:
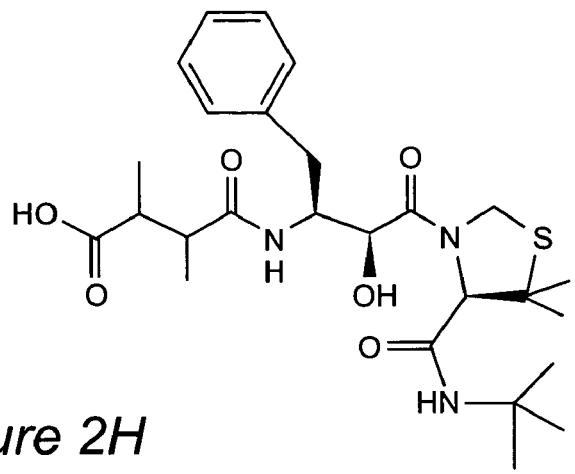
Figure 2I:
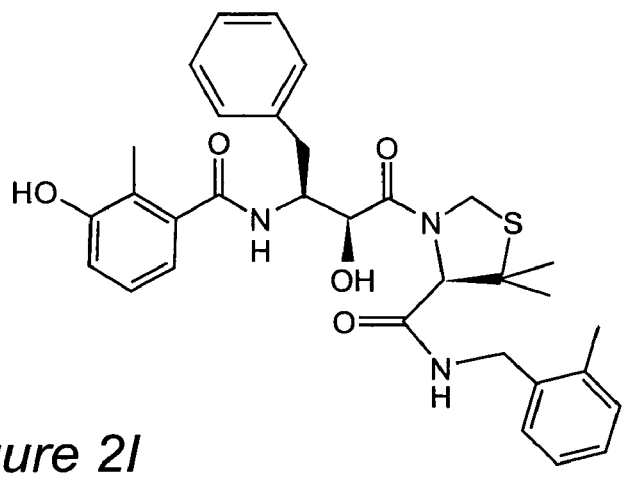
Figure 2J:
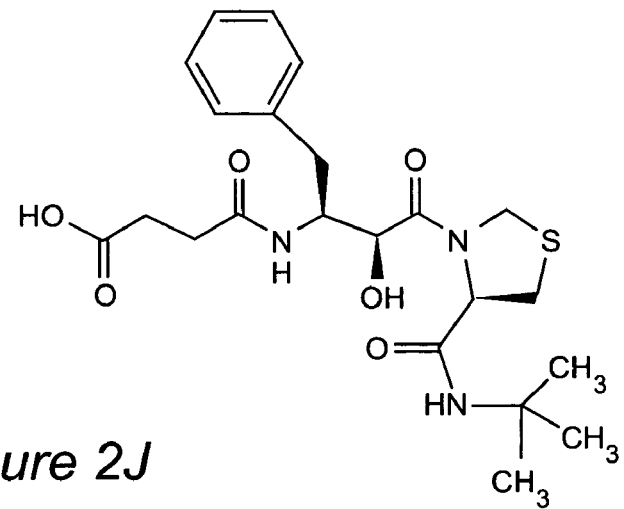
Figure 5G:
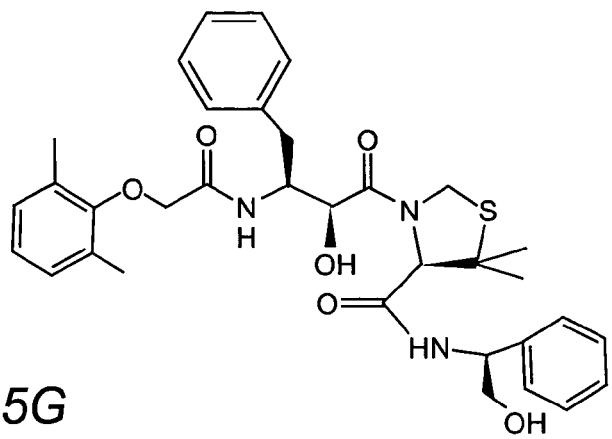
Figure 5H:
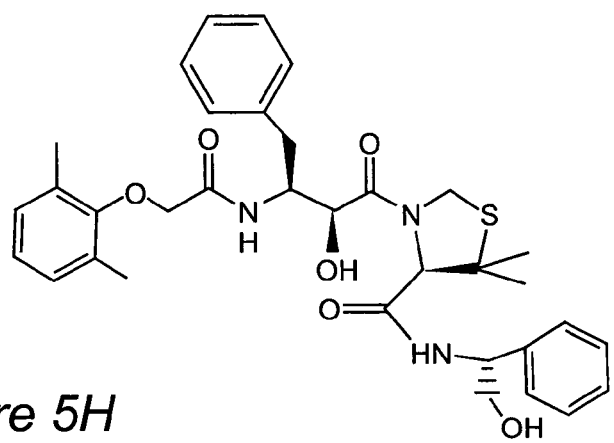
Figure 5I:
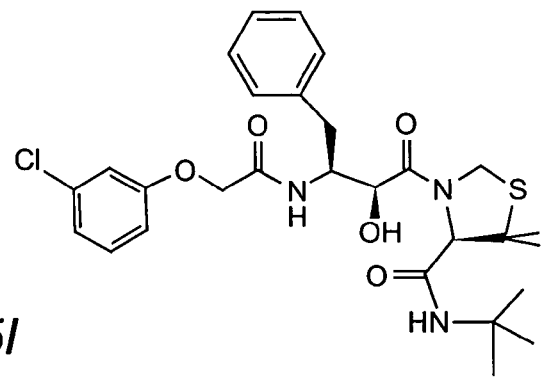
Figure 5J:
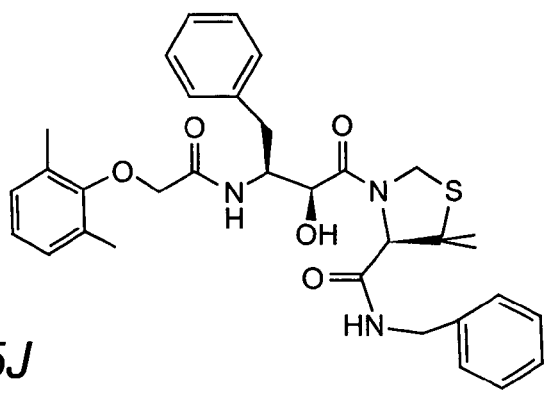
Figure 6A:
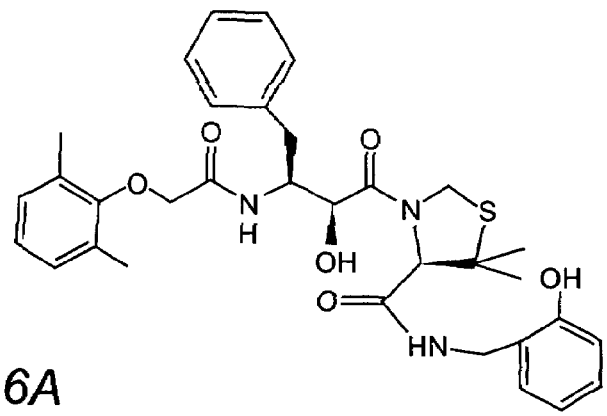
FIG. 6. Chemical structures of: A, KNI-10047; B, KNI-10048; C, KNI-10049; D, KNI-10050; E, KNI-10051; F, KNI-10052; G, KNI-10053; Hl, KNI-10054; I, KNI-10055; J, KNI-10056; and K, KNI-10057.
Figure 6B:
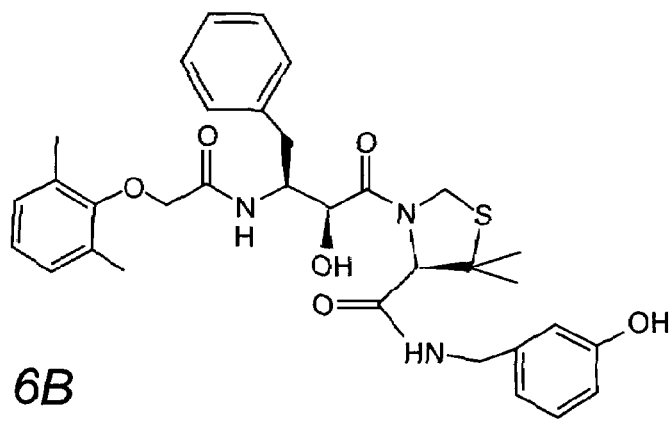
Figure 6C:
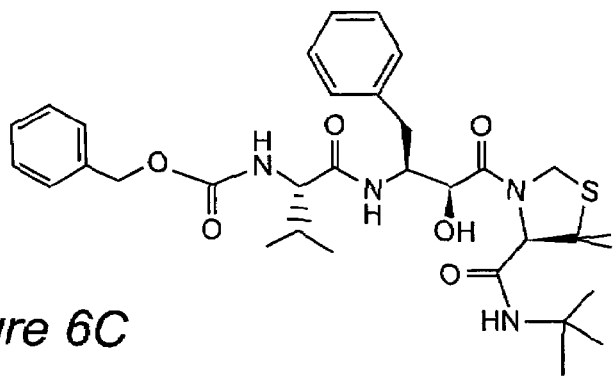
Figure 6D:
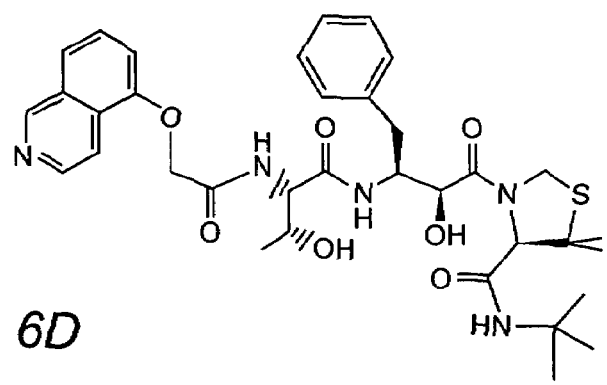
Figure 6E:
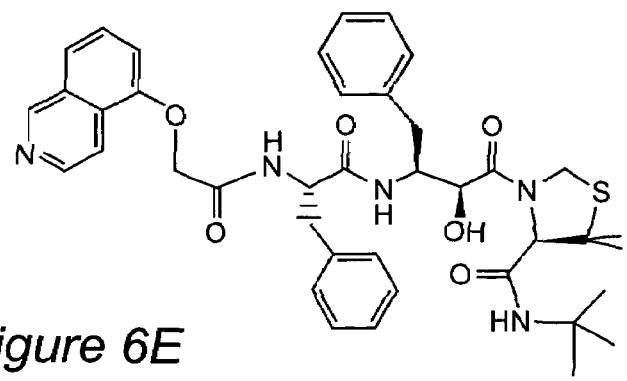
Figure 6F:
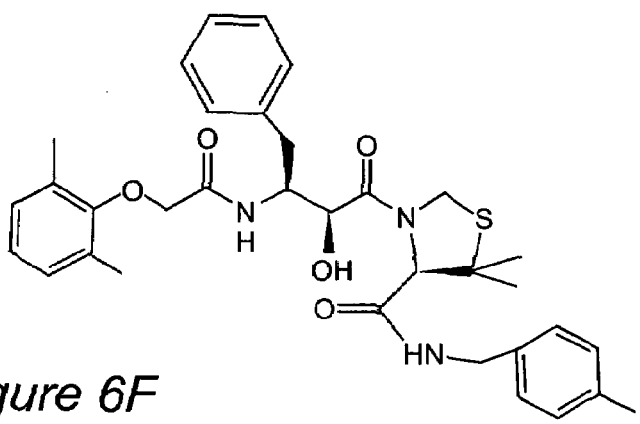
Figure 6G:
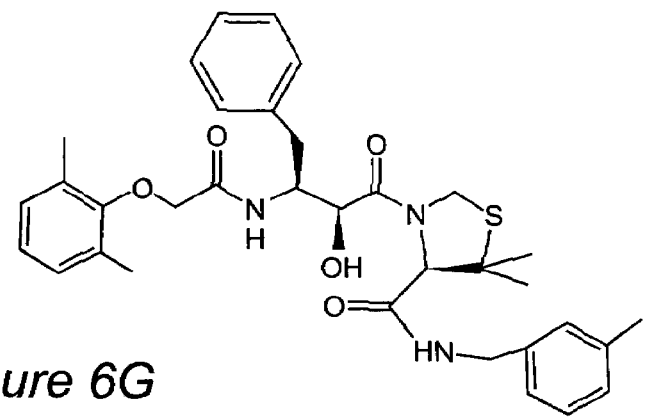
Figure 6H:
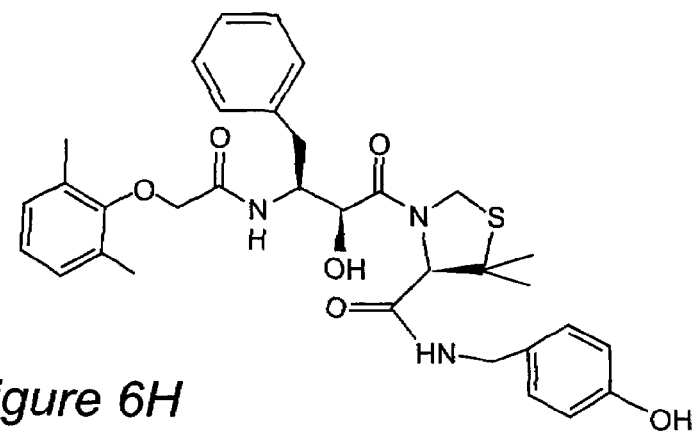
Figure 6I:
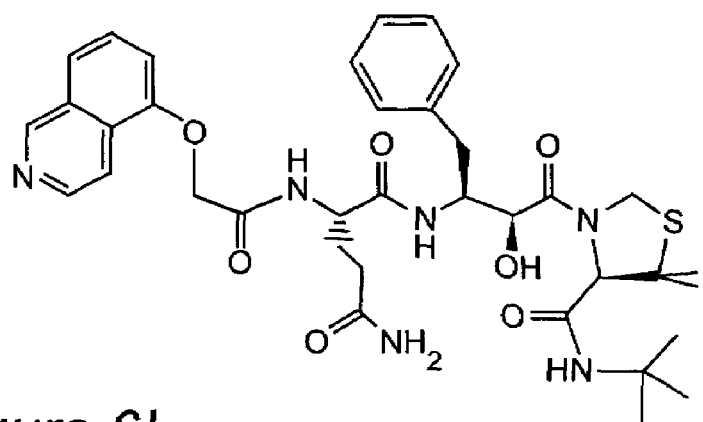
Figure 6J:
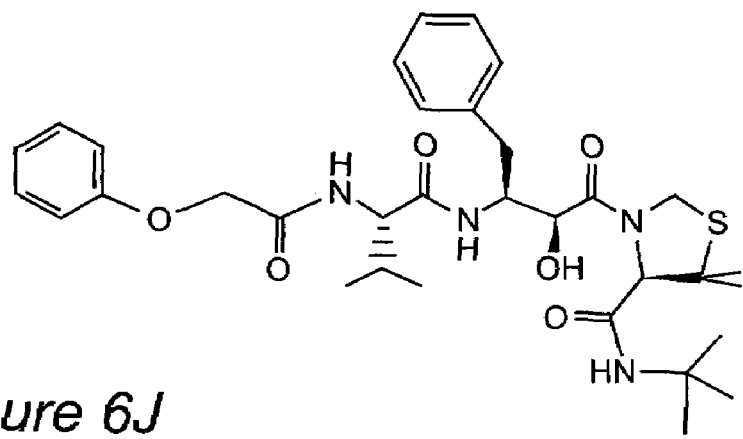
Figure 6K:
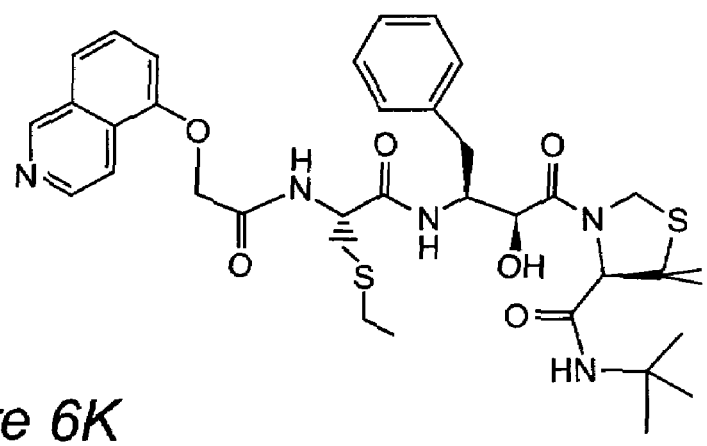

| Compound | $K_i$ Plasmepsin II (nM) | $K_i$ Cathepsin D (nM) | Discrimination Factor: Fold Selectivity for Plasmepsin II over Cathepsin D | Figure Reference Number |
|---|---|---|---|---|
| KNI-727 | 70 | 1600 | ~23 | FIG. 2B |
| KNI-764 | 30 | 201 | ~7 | FIG. 2I |
| KNI-840 | 20 | 80 | 4 | FIG. 3B |
| KNI-227 | 36 | 1773 | ~49 | FIG. 3D |
| KNI-10006 | 0.5 | 2 | 4 | FIG. 3J |
| KNI-10026 | 15 | 105 | 7 | FIG. 4G |
| KNI-10030 | 11 | 111 | ~10 | FIG. 5A |
| KNI-10033 | 3 | 40 | ~13 | FIG. 5D |
| KNI-10043 | 22 | 53 | 2.4 | FIG. 5G |
| KNI-10053 | 41 | 360 | ~9 | FIG. 6G |

Example 3

Evaluation of the Ability of KNI Compounds to Kill the Malaria Parasite

Figure 9:
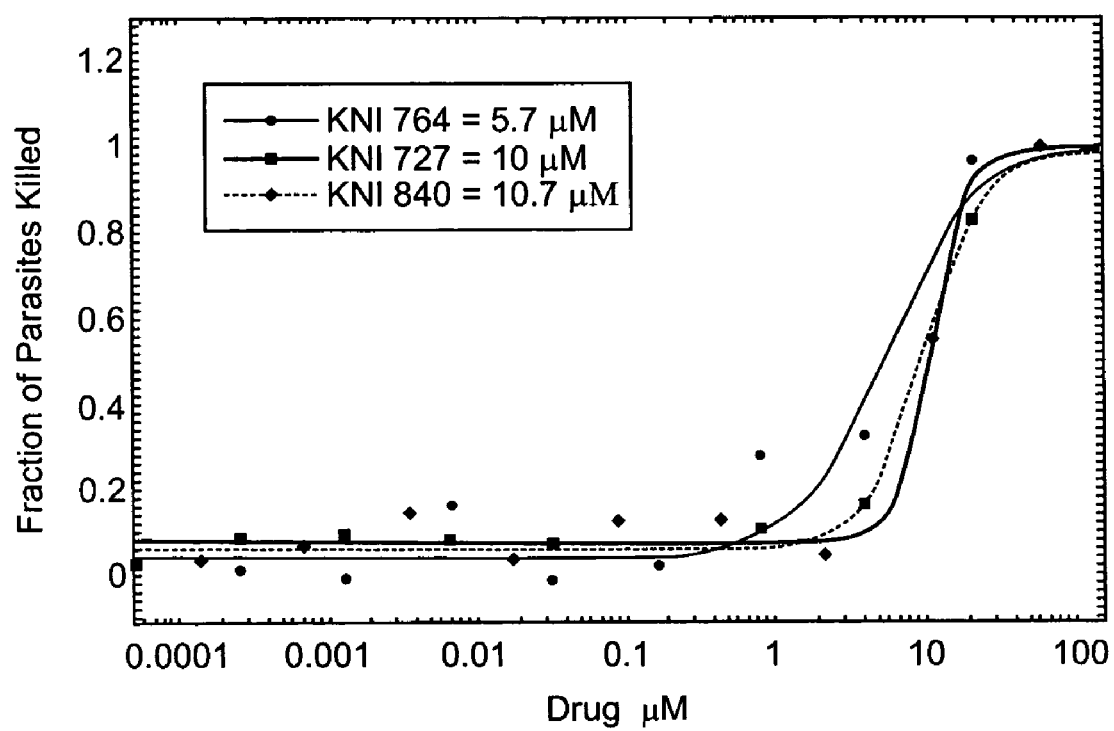
FIG. 9. Percent of malarial parasites killed in malaria infected human erythrocytes by KNI-727, KNI-764 and KNI-840. Analysis of the data yields an IC50 of 5.7 mM for KNI-764 and 10 mM for KNI-727 and KNI-840 respectively.

The ability of some KNI compounds to kill the malaria parasite was evaluated by measuring the IC50 in a malaria-infected human red blood cell assay. Activity was determined by measuring the incorporation of [$^3$H]hypoxanthine. Briefly, chloroquine-sensitive *Plasmodium falciparum* (NF54) were maintained in a 2.4% suspension of type O$^+$ human erythrocytes in RPMI 1640, supplemented with 25 mM HEPES, 27 mM NaHCO$_3$, and 10% heat-inactivated human type O$^+$ serum, under 3% O$_2$, 4% CO$_2$, and 93% N$_2$. 20 mM stock solutions of KNI-764 and KNI-727 and KNI-840 were prepared in DMSODMSO solutions were diluted 500 fold in medium, serially diluted in 0.2% DMSO in medium, then 100

µl aliquots were pipetted into microtiter plate wells. Provisional $EC_{50}$ values were obtained in a survey of ten 5-fold dilutions yielding final concentrations (in quadruplicate) of 0.00001-20 µM. Plates included 8 wells of no drug controls (4 with and 4 without DMSO) and 4 wells in uninfected erythrocytes. Parasite culture (0.25% parasitemia in 2.3% hematocrit, 100 µl per well) was added and the plate was incubated for 48 hours prior to the addition of 0.6 µCi [$^3$H]hypoxanthine and subsequent 20 h incubation. Cells were harvested onto GF-C glass filters. The filters were washed four times with 3 ml water per sample spot, dried under a heat lamp, and counted in scintillation cocktail. Decays per minute values were downloaded and analyzed in order to yield the mean and standard deviation at each drug concentration. Dose-response curves were fit to the experimental data in order to obtain the drug concentration that kills 50% of parasites (IC50). The results obtained for KNI-727, KINI-840 and KNI-764 are shown in FIG. 9.

As can be seen, KNI-727, KNI-764, and KNI-840 all are able to kill the malaria parasite with low IC50 values of 5.7 µM, 10 µM and 10 µM, respectively. This example demonstrates that KNI compounds are able to kill malaria parasites in infected human erythrocyte cultures.

Example 4

The Binding Energetics of KNI Compounds

Figure 1B:
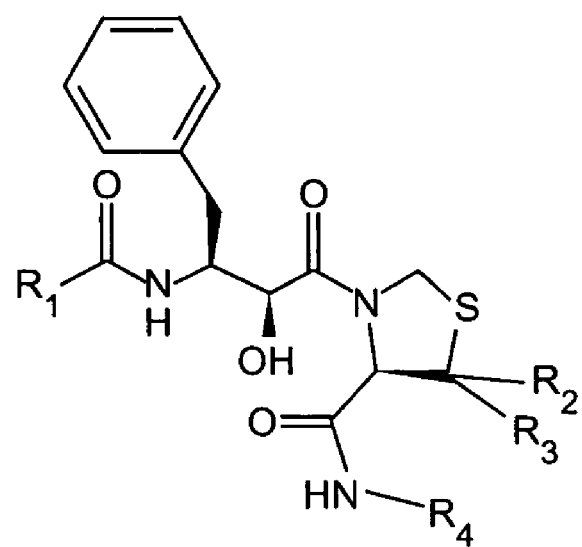

The allophenylnorstatine scaffold was chosen as a prospective plasmepsin inhibitor because of its close similarity to the primary cleavage site of plasmepsin II, the peptide bond between Phe 33 and Leu 34 in the alpha chain of hemoglobin, and the potential for the introduction of different types of functional groups (FIG. 1B). The allophenylnorstatine scaffold contains four different positions (labeled R1-R4 in the structure in FIG. 1B) where different chemical functional groups can be introduced in order to improve binding affinity and selectivity. Using the standard enzymatic nomenclature, the allophenylnorstatine moiety in these compounds corresponds to the P1 position, R1 corresponds to the P2 position, the thioproline group together with R2 and R3 correspond to the P1' position and R4 corresponds to the P2' position.

The binding energetics of a library of allophenylnorstatine-based compounds (KNI library) have been measured as described above. The binding enthalpy of a subset of these compounds was determined high sensitivity isothermal titration calorimetry. All the samples were found to bind plasmepsin II with a favorable binding enthalpy ranging from −1.5 to −7.4 kcal/mol. The binding of KNI compounds to Plasmepsin II is both enthalpically and entropically favorable. This is a very important characteristic from the point of view of further optimization of these compounds since it reflects the fact that not a single type of force (enthalpy or entropy) is driving the binding reaction as is the case with other inhibitors (Todd et al., 2000). Also, a well balanced distribution of binding forces lowers the susceptibility of inhibitors to changes in the environment or in the target molecule, thus making them less prone to drug resistance issues. By displaying a favorable binding enthalpy, the binding entropy does not have to exhibit extreme values in order to achieve high binding affinity. The implication is that the compounds can be allowed to have certain flexibility that allows them to accommodate to variations in the target such as those found in drug-resistant mutants or naturally-occurring amino acid polymorphisms among the plasmepsins.

Example 5

Comparison with Previously Reported Compounds

The Ki of KNI-10006 for Plasmepsin II is 0.5 mM, being the highest so far. The $K_i$ of KNI-227 and KNI-727 for plasmepsin II are 30 and 60 nM with a discrimination factor of 50 and 22 with regard to Cathepsin D. In addition, KNI-727 has an IC50 of 10 µM measured in the malaria-infected red blood cell assay. Previously Haque et al. (Haque et al., 1999) reported results on a series of plasmepsin II inhibitors. The best inhibitor had a $K_i$ of 4 nM, however the discrimination factor between plasmepsin II and Cathepsin D was only 14. Silva et al (Silva et al., 1996) reported on a peptide-based inhibitor with a $K_i$ of 0.6 nM and a discrimination factor of 35, however the reported IC50 in a red blood cell assay was around 20 µM. The discrimination factor for KNI-227 and KNI-727 are also significantly better than the discrimination factor of 6.4 obtained with the best inhibitor selected from an encoded statine combinatorial library (Carrol et al., 1998). Thus, the combination of high affinity, high selectivity and high biological inhibition activity makes allophenylnorstatine-based compounds novel and powerful plasmepsin II inhibitors. Specific compounds such as KNI-727 and also provides important prototypes for the further development of new antimalarial compounds by further refinement of their structures.

While the invention been described in terms of its preferred embodiments skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Butler, D., Maurice, J. & O'Brien, C. (1997). Time to put malaria control on the global agenda. Nature 386, 535-541.

Carrol, C. D., Patel, H., Johnson, T. O., Guo, T., Orlowski, M., He, Z. M., Cavallaro, C. L., Guo, J., Oksman, A., Gluzman, I. Y., Connelly, J., Chelsky, D., Goldberg, D. E. & Dolle, R. E. (1998). Identification of potent inhibitors of Plasmodium falciparum plasmepsin II from an encoded statine combinatorial library. Bioorganic & Medicinal Chemistry Letters 8, 2315-2320.

Coombs, G. H., Goldberg, D. E., Klemba, M., Berry, c., Kay, J., Mottram, J. C., 2001. Aspartic proteases of Plasmodium falciparum and other parasitic protozoa as drug targets. Trends in Parasitology 17, 532-37.

Francis, S. E., Banerjee, R. & Goldberg, D. E. (1997a). Biosynthesis and maturation of the malaria aspartic hemoglobinases Plasmepsins I and II. J. Biol. Chem. 272, 14961-14968.

Francis, S. E., Sullivan, D. J. & Goldberg, D. E. (1997b). Hemoglobin metabolism in the malaria parasite Plasmodium Falciparum. Annu. Rev. Microbiol. 51, 97-123.

Goldberg, D. E. (1993). Hemoglobin degradation in infected red blood cells. Semin. Cell. Biol. 4, 355-361.

Haque, T. S., Skillman, G., Lee, C. E., Habashita, H., Gluzman, I. Y., Ewing, T. J. A., Goldberg, D. E., Kuntz, I. D. & Ellman, J. A. (1999). Potent, low-molecular-weight non-peptide inhibitors of malarial aspartyl protease plasmepsin II. J. Med. Chem. 42, 1428-1440.

Kiso, Y. (1996). Design and synthesis of substrate-based peptidomimetic human immunodeficiency virus protease inhibitors containing the hydroxymethylcarbonyl isostere. *Biopolymers (Peptide Science)* 40, 235-244.

Kiso, Y. (1998). Design and synthesis of a covalently linked HIV-1 protease dimer analog and peptidomimetic inhibitors. *J. Synthetic Org. Chem* (Japan) 56, 32-43.

Kiso, Y., Matsumoto, H., Mizumoto, S., Kimura, T., Fujiwara, Y. & Akaji, K. (1999). Small dipeptide-based HIV protease inhibitors containing the hydroxymethylcarbonyl isoterre as an ideal transition state mimic. *Biopolymers* 51, 59-68.

Luker, K. E., Francis, S. E., Gluzman, 1.Y. & Goldberg, D. E. (1996). Kinetic analysis of plasmepsins I and II, aspartic proteases of the *Plasmodium falciparum* digestive vacuole. *Mol. Biochem. Parasitology* 79, 71-78.

Miller, L. H., Good, M. F. & Milon, G. (1994). Malaria pathogenesis. *Science* 264, 1878-1883.

Mimoto, T., Kato, R., Takaku, H., Nojima, S., Terashima, K., Misawa, S., Fukazawa, T., Ueno, T., Sato, H., Shintani, M., Kiso, Y. & Hayashi, H. (1999). Structure-Activity Relationship of Small-Sized HIV protease inhibitors containing allophenylnorstatine. *J. Med. Chem.* 42, 1789-1802.

Silva, A. M., Lee, A. Y., Gulnik, S. V., Majer, P., Collins, J., Bhat, T. N., Collins, P. J., Cachau, R. E., Luker, K. E., Gluzman, I.Y., Francis, S. E., Oksman, A., Goldberg, D. E. & Erickson, J. W. (1996). Structure and inhibition of plasmepsin II, a hemoglobin-degrading enzyme from *Plasmodium falciparum. Proc. NAtl. Acad. Sci.* (*USA*) 93, 10034-10039.

Todd, M. J., Luque, I., Velazquez-Campoy, A. & Freire, E. (2000). The Thermodynamic Basis of Resistance to HIV-1 Protease Itlliibition. Calorimetric Analysis of the V82F/184V Active Site Resistant Mutant. *Biochemistry* 39, 11876-11883.

Wyler, D. J. (1993). Malaria Overview and Update. *Clin. Infect. Dis.* 16, 449-458.

We claim:

1. A method of inhibiting a plasmepsin, comprising, exposing said plasmepsin to an allophenylnorstatine-based compound, wherein said step of exposing results in inhibition of said plasmepsin.

2. The method of claim 1, wherein said plasmepsin is selected from the group consisting of Plasmepsin I, Plasmepsin II, Plasmepsin IV, and histo-aspartic proteinase (HAP).

3. The method of claim 1, wherein said plasmepsin is Plasmepsin II.

4. The method of claim 1, wherein said allophenylnorstatine-based compound with following structure is substituted at positions $R_1$, $R_2$, $R_3$ and $R_4$ such that

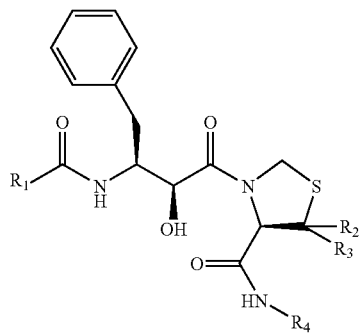

$R_1$ is A or A-B, wherein A is selected from the group consisting of a linear or branched aliphatic hydrocarbon having 1-7 carbon atoms which may be substituted by at least one carboxyl group;

a 6-membered monocyclic hydrocarbon which may be substituted with a substituent selected from the group consisting of alkyl, amino, alkylamino, arylamino, hydroxy, alkyloxy and halogen atom;

a bicyclic hydrocarbon having 7-10 carbon atoms which may be substituted by a substituent selected from the group consisting of alkyl, amino, alkylamino, arylamino, hydroxy, alkyloxy and halogen atom; and a monocyclic or bicyclic hydrocarbon wherein more than one carbon atom is substituted; and B is selected from the group consisting of —CO—NH—CH(Ra)—, —CH$_2$—CO—NH(Ra)—, —O—CH$_2$—CO—NH—CH(Ra)—, —OCH$_2$— and —CH$_2$O, wherein Ra is a linear or branched aliphatic hydrocarbon having 1-7 carbon atoms that may be substituted with a substituent selected from the group consisting of alkylthio, hydroxy, aromatic hydrocarbons, and carbamoyl;

R2 is hydrogen or a linear or branched aliphatic hydrocarbon having 1-6 carbons;

R3 is hydrogen or a linear or branched aliphatic hydrocarbon having 1-6 carbons; and R4 is selected from the group consisting of a linear or branched aliphatic hydrocarbon having 1-10 carbons which can be substituted with a substituent selected from the group consisting of aryl, hydroxyl, alkyloxy, amino, alkylamino and halogen;

a monovalent moiety derived from an aromatic mono- or bicyclic hydrocarbon having 12 or fewer carbons, and wherein said moiety can be substituted by a substituent selected from the group consisting of alkyl, aryl, hydroxyl, alkyloxy, amino, alkylamino, or halogen;

a monovalent moiety derived from a heterocycle in which more than one carbon atom is substituted with a hetero atom, wherein said moiety can be substituted by a substituent selected from the group consisting of alkyl, aryl, hydroxyl, alkyloxy, amino, alkylamino, and halogen.

5. The method of claim 1, wherein said allophenylnorstatine-based compound is a di-peptide.

6. The method of claim 1, wherein said allophenylnorstatine-based compound is a tri-peptide.

7. The method of claim 1, wherein said allophenylnorstatine-based compound exhibits a Ki for Plasmepsin II from *Plasmodium falciparum* in the nanomolar to subnanomolar range.

8. The method of claim 1, wherein said allophenylnorstatine-based compound is selected from the group consisting of KNI-727, KNI-764, KNI-840, KNI-227, KNI-10006, KNI-10026, KNI-10033, KNI-10043 and KNI-10053.

9. The method of claim 1, wherein said plasmepsin is Plasmepsin II that originates from a genus species of *Plasmodium* selected from the group consisting of *P. falcikarum, P. vivax, P. malariae* or *P. ovale*.

10. The method of claim 4, wherein

A is selected from the group consisting of HOOC—CRbRb—CRbRb— wherein Rb is hydrogen or methyl; phenyl; 3-hydroxy-2-methylphenyl; 2,6-dimethylphenyl; 3-chlorophenyl; 3-phenylaminophenyl; 3-dimethylaminophenyl; 1-naphtyl; 2-naphtyl; 2-pyridyl; 5-isoquinolyl; 2-quinolyl; 2-benzofuranyl; and 2-chromonyl;

B is selected from the group consisting of —CO—NH—CH(Ra)—, —CH$_2$—CO—NH(Ra)—, —O—CH$_2$—CO—NH—CH(Ra)—, —OCH$_2$— and —CH$_2$O, wherein Ra is propyl, isopropyl, isobutyl, sec-butyl, methylthiomethyl, methylthioethyl, ethylthiomethyl, phenylmethyl, carbamoylethyl, or 1-hydroxyethyl;

$R_2$ is hydrogen or methyl;

$R_3$ is hydrogen or methyl; and $R_4$ is selected from the group consisting of benzyl; tert-butyl; 2-hydroxybenzyl; 3-hydroxybenzyl; 4-hydroxybenzyl; 2-hydroxyindanylyl; 2-hydroxy-1-phenethyl; 1-indanyl; 2-methoxybenzyl; 3-methoxybenzyl; 4-methoxybenzyl; 4-methoxyphenethyl; 2-methylbenzyl; 3-methylbenzyl; 4-methylbenzyl; naphtyl; and 1-phenethyl.

11. The method of claim 4, wherein R2 and R3 are selected from the group consisting of hydrogen, methyl and ethyl.

12. The method of claim 4, wherein R4 is aminoindanol.

13. The method of claim 4, wherein said allophenylnorstatine-based compound is a tri-peptide and: R1 is isoquinolineoxyacetyl at position P3 and methylthioalanine at position P2, R2 and R3 are methyl, and R4 is selected from the group consisting of (1S,2R)-aminoindanol and tert-butylamine.

14. The method of claim 5, wherein R1 is selected from the group consisting of methylphenol, methylated derivatives of carboxyl, and chlorobenzene.

15. The method of claim 6, wherein R1 is selected from the group consisting of methylphenol, methylated derivatives of carboxyl, chlorobenzene, valine, leucine, isoleucine, methionine, phenylalanine, glutamine, and derivatives thereof.

16. The method of claim 10, wherein said plasmepsin is Plasmepsin II and $R_1$ is selected from the group consisting of 2,6-dimethylphenyl-$OCH_2$—, 3-hydroxy-2-methylphenyl and 5-isoquinolyl-O—$CH_2$—CO—NH—CH(Ra) where Ra is methylthiomethyl;

$R_2$ is methyl;

$R_3$ is methyl; and $R_4$ is selected from the group consisting of benzyl; tert-butyl; 2-hydroxybenzyl; 3-hydroxybenzyl; (1S,2R)-2-hydroxyindanyl; (1R,2S)-2-hydroxyindanyl; (S)-2-hydroxy-1-phenethyl; (S)-indanyl; 4-methoxyphenethyl; 2-methylbenzyl; 3-methylbenzyl; naphthyl; and (R)-1-phenethyl.

* * * * *